United States Patent
Hangai et al.

(10) Patent No.: US 7,641,339 B2
(45) Date of Patent: Jan. 5, 2010

(54) OPHTHALMOLOGIC INFORMATION PROCESSING APPARATUS AND OPHTHALMOLOGIC EXAMINATION APPARATUS

(75) Inventors: Masanori Hangai, Kyoto (JP); Nagahisa Yoshimura, Kyoto (JP); Yijun Huang, Pleasantvile, NY (US); Ryoichi Nadachi, Fujimino (JP)

(73) Assignee: Kabushiki Kaisha Topcon, Itabashi-Ku (JP)

( * ) Notice: Subject to any disclaimer, the term of this patent is extended or adjusted under 35 U.S.C. 154(b) by 247 days.

(21) Appl. No.: 11/882,236

(22) Filed: Jul. 31, 2007

(65) Prior Publication Data
US 2009/0033870 A1 Feb. 5, 2009

(51) Int. Cl.
*A61B 3/14* (2006.01)
*A61B 3/10* (2006.01)
*A61B 3/00* (2006.01)

(52) U.S. Cl. .................. 351/206; 351/205; 351/221; 351/245

(58) Field of Classification Search .......... 351/205–246
See application file for complete search history.

(56) References Cited

U.S. PATENT DOCUMENTS

| 5,828,439 | A | * | 10/1998 | Ueno | .......................... | 351/205 |
| 7,370,966 | B2 | * | 5/2008 | Fukuma et al. | ............. | 351/205 |
| 2005/0018133 | A1 | | 1/2005 | Huang et al. | | |
| 2006/0176448 | A1 | | 8/2006 | Van de Velde | | |

FOREIGN PATENT DOCUMENTS

| EP | 1236432 | 9/2002 |
| EP | 1340451 | 9/2003 |
| EP | 1775545 | 4/2007 |
| JP | 11-325849 | 11/1999 |
| JP | 2000-262471 | 9/2000 |
| JP | 2002-139421 | 5/2002 |
| JP | 2002-253502 | 9/2002 |
| JP | 2003-000543 | 1/2003 |
| JP | 2003-164424 | 6/2003 |
| JP | 2005-102946 | 4/2005 |

OTHER PUBLICATIONS

Johann Sjöstrand et al. "Morphometric Study of the Displacement of Retinal Ganglion Cells Subserving Cones Within the Human Fovea" Clinical Investigation vol. 237, 1999, pp. 1014-1023, Sep. 1999.
European Searc h Report,, Dec. 5, 2008, issued in EP 08 01 0029.

* cited by examiner

*Primary Examiner*—Mohammed Hasan
(74) *Attorney, Agent, or Firm*—Edwards Angell Palmer & Dodge LLP

(57) ABSTRACT

An ophthalmologic examination apparatus 1 projects a light onto a fundus oculi, detects the reflected light thereof, and forms a 3-dimensional image that represents the morphology of a retina based on the detected results. A stimulation-position specifying part 233 specifies, in the 3-dimensional image, a plurality of stimulation positions that correspond to a plurality of stimulation points Pi in a visual-field examination. A layer-thickness measuring part 235 analyzes the 3-dimensional image to find the layer thickness of the retina at each stimulation position. In addition, a displacement calculation part 234 specifies a related position of the stimulation position. A layer-thickness measuring part 235 finds the layer thickness of the retina at the related position.

12 Claims, 12 Drawing Sheets

FIG. 8

| DISPLACEMENT OF CONE (mm/deg) | TOTAL DISPLACEMENT (mm/deg) | DISPLACEMENT OF GANGLIOCYTE (mm/deg) | AREA RATIO ($A_C / A_{RGC}$) |
|---|---|---|---|
| 0.25/0.90 | 0.31/1.12 | 0.56/2.02 | 0.44 |
| 0.50/1.80 | 0.36/1.29 | 0.86/3.09 | 0.58 |
| 1.00/3.60 | 0.34/1.21 | 1.34/4.81 | 0.75 |
| 1.50/5.40 | 0.20/0.74 | 1.70/6.14 | 0.88 |
| 2.00/7.20 | 0.10/0.37 | 2.10/7.57 | 0.95 |

OPHTHALMOLOGIC INFORMATION PROCESSING APPARATUS AND OPHTHALMOLOGIC EXAMINATION APPARATUS

BACKGROUND OF THE INVENTION

The present invention is related to an ophthalmologic information-processing apparatus and an ophthalmologic examination apparatus that are used for examinations in the field of ophthalmology.

In the examinations used in the field of ophthalmology, there is a visual field examination for measuring the visual field of an eye. The visual-field examination is carried out for diagnosing diseases in which abnormalities of the visual field occur, such as glaucoma, retinal pigmentary degeneration, central chorioretinopathy, optic neuritis, and macular hole. Abnormalities of the visual field include stenosis, hemianopia, scotoma, and the like.

For the visual-field examination, a dynamic perimeter for measuring dynamic visual field and a static perimeter for measuring static visual field are used (e.g. cf. Japanese Unexamined Patent Publications JP-A 2000-262471, JP-A 2002-253502, and JP-A 2003-164424). The dynamic perimeter is referred to as an automated perimeter or the like. In recent years, the static perimeter has mainly been used because of an advantage thereof that it is possible to automatically carry out measurements without the need to move a visual target presented on the eye.

The static perimeter sequentially projects a spotlight onto a plurality of stimulation points of a fundus oculi of a fixed eye, makes a subject respond as to whether he/she perceives the light for each stimulation point, and records the response result (sensitivity threshold).

The plurality of stimulation points are arranged in a predetermined pattern. A typical example of the arrangement pattern of the stimulation points is one in which the stimulation points are arranged at intervals of two degrees within a ten-degree range of view from the fovea centralis (fixed position).

In addition, a perimeter comprising a function of imaging a fundus oculi image is also known (e.g. c.f. Japanese Unexamined Patent Publication JP-A2005-102946). With this perimeter, it is possible to designate a stimulation point on a fundus oculi image. In addition, it is also possible to present the stimulation points on the fundus oculi image.

The causes for abnormalities of the visual field include abnormalities in the eyeball, abnormalities of the optic nerve, abnormalities of the optic chiasm, abnormalities in areas beyond the optic chiasm, and other abnormalities (such as psychogenic disorders). Abnormalities in the eyeball may be detected as morphological abnormalities of the retina. As an apparatus for detecting the morphological abnormalities of the retina, an optical image measuring apparatus has recently been gathering attention.

The optical image measuring apparatus is an apparatus to which OCT (Optical Coherence Tomography) technology is applied. The OCT technology is a technology of using optical beams to form images that represent the surface morphology or the internal morphology of an object to be measured. Unlike X-ray CT scanner, OCT technology is not invasive to the human body, so that its development is being highly anticipated, especially in the medical field.

Japanese Unexamined Patent Publication JP-A 11-325849 discloses an optical image measuring apparatus having a configuration in which: a measuring arm scans an object by using a rotating mirror (Galvano mirror); a reference mirror is installed on a reference arm; at the exit thereof, an interference device, in which the intensity of lights emerging from the interference of light fluxes from the measuring arm and the reference arm is also analyzed by a spectroscope, is utilized; and the reference arm is provided with an apparatus for changing a reference light flux phase by discontinuous values in a stepwise fashion.

The optical image measuring apparatus disclosed in JP-A 11-325849 uses the so-called "Fourier Domain OCT technique." In other words, the apparatus irradiates an object to be measured with a beam of low-coherence light, obtains the spectral intensity distribution of the reflected light, and performs Fourier transform thereof, thereby converting the morphology of the object to be measured in the depth direction (z direction) into an image.

Furthermore, the optical image measuring apparatus described in JP-A 11-325849 comprises a Galvano mirror for scanning optical beams (signal lights), thereby being capable of forming an image of a desired region to be measured in the object to be measured. Incidentally, this optical image measuring apparatus is adapted to scan optical beams only in one direction (x direction) perpendicular to the z direction, so that the formed image is a 2-dimensional tomographic image in the depth direction (z direction) along the scanning direction (x direction) of the optical beams.

In addition, Japanese Unexamined Patent Publication JP-A 2002-139421 discloses a technology of: forming a plurality of 2-dimensional tomographic images in the horizontal direction by scanning the signal lights in both the horizontal and vertical directions; obtaining, based on the plurality of tomographic images, 3-D tomographic information within a measurement range; and converting it into an image. Possible examples of this 3-D imaging include a method in which a plurality of tomographic images are displayed side by side in a vertical line (referred to as stack data or the like), and a method in which a 3-dimensional image is formed by applying a rendering process to a plurality of tomographic images.

Moreover, Japanese Unexamined Patent Publication JP-A 2003-543 discloses a configuration in which such an optical image measuring apparatus is applied in the field of ophthalmology.

As described above, an abnormality of the visual field and a morphological abnormality of the retina may be related to each other. Conventionally, it has been possible to individually grasp an abnormality of the visual field and a morphological abnormality of the retina, but it has not been possible to grasp the morphology of the retina at a stimulation point in a visual-field examination. Therefore, it has also not been possible to grasp an abnormality of the visual field and a morphological abnormality of the retina in the corresponding manner.

Incidentally, with the perimeter described in JP-A 2005-102946, it is possible to grasp, by referring to a fundus oculi image, in what site of the fundus oculi a visual field has been measured, but it is not possible to grasp a morphological abnormality of the retina, especially an abnormality inside the retina. Therefore, even with this perimeter, it is not possible to grasp the correspondence between an abnormality of the visual field and a morphological abnormality of the retina.

The present invention has been achieved to solve these problems, and an object thereof is to provide a technology for enabling grasp of the correspondence between the state of visual-field functions and the morphology of a retina.

In order to achieve the above object, in a first aspect of the present invention, an ophthalmologic information-processing apparatus comprises: an accepting part configured to accept a 3-dimensional image representing a morphology of a retina; a specifying part configured to specify, in the 3-dimensional image, a plurality of positions corresponding to a plurality of stimulation points in a visual-field examination; and an analyzing part configured to analyze the 3-dimensional image and find a layer thickness of the retina at each of the plurality of positions.

Further, in a second aspect of the present invention, the ophthalmologic information-processing apparatus is characterized in that: the specifying part specifies, for each of the plurality of positions, a new position related to the position; and the analyzing part analyzes the 3-dimensional image and finds the layer thickness of the retina at the new position.

Furthermore, in a third aspect of the present invention, the ophthalmologic information-processing apparatus is characterized in that: the new position is a position where a ganglion cell, which receives signals from a cone existing at the position, exists.

Still further, in a fourth aspect of the present invention, the ophthalmologic information-processing apparatus is characterized in that: the specifying part comprises a storing part configured to previously store association information that associates a position of the cone and a position of the ganglion cell, refer to the association information for each of the plurality of positions, and find the position of the ganglion cell corresponding to the position of the cone, as the new position.

Still further, in a fifth aspect of the present invention, an ophthalmologic information-processing apparatus comprises: an accepting part configured to accept a 3-dimensional image representing a morphology of a retina; a designating part configured to designate a position in the 3-dimensional image; a specifying part configured to specify a new position related to the designated position; and an analyzing part configured to analyze the 3-dimensional image and find a layer thickness of the retina at the new position.

Still further, in a sixth aspect of the present invention, the ophthalmologic information-processing apparatus is characterized in that: the new position is a position where ganglion cell, which receives signals from cone existing at the designated position, exists.

Still further, in a seventh aspect of the present invention, the ophthalmologic information-processing apparatus is characterized in that: the specifying part comprises a storing part configured to previously store association information that associates a position of the cone and a position of the ganglion cell, refer to the association information, and find the position of the ganglion cell corresponding to the designated position, as the new position.

Still further, in an eighth aspect of the present invention the ophthalmologic information-processing apparatus is characterized in that: the specifying part sets, for each of the plurality of positions, an image region including the position; and the analyzing part finds the layer thickness at two or more positions in the image region and finds the layer thickness of the retina at the positions based on the layer thickness at the two or more positions.

Still further, in a ninth aspect of the present invention, the ophthalmologic information-processing apparatus is characterized in that: the specifying part sets an image region including the new position; and the analyzing part finds the layer thickness at two or more positions in the image region, and finds the layer thickness of the retina at the new position based on the layer thickness at the two or more positions.

Still further, in a tenth aspect of the present invention, the ophthalmologic information-processing apparatus is characterized in that: the analyzing part finds an average value of the layer thickness at the two or more positions.

Still further, in an eleventh aspect of the present invention, the ophthalmologic information-processing apparatus is characterized in that: the accepting part accepts examination results of a visual-field examination; and the analyzing part comprises a comparing part configured to compare the layer thickness of the retina and the examination results, and also comprises an output part configured to output the comparison results.

Still further, in a twelfth aspect of the present invention, an ophthalmologic examination apparatus comprises: an image forming part configured to project a light onto a fundus oculi, detect the reflected light thereof, and form a 3-dimensional image representing a morphology of a retina based on the detected results; a specifying part configured to specify, in the 3-dimensional image, a plurality of positions corresponding to a plurality of stimulation points in a visual-field examination; and an analyzing part configured to analyze the 3-dimensional image and find a layer thickness of the retina at each of the plurality of positions.

Still further, in a thirteenth aspect of the present invention, the ophthalmologic examination apparatus is characterized in that: the specifying part specifies, for each of the plurality of positions, a new position related to the position; and the analyzing part analyzes the 3-dimensional image and finds the layer thickness of the retina at the new position Still further, in a fourteenth aspect of the present invention, an ophthalmologic examination apparatus comprises: an image forming part configured to project a light onto a fundus oculi, detect the reflected light thereof, and form a 3-dimensional image representing a morphology of a retina based on the detected results; a designating part configured to designate a position in the 3-dimensional image; a specifying part configured to specify a new position related to the designated position; and an analyzing part configured to analyze the 3-dimensional image and find a layer thickness of the retina at the new position.

According to the present invention, the layer thickness of the retina at a stimulation point in a visual-field examination can be measured, so that it is possible to grasp the correspondence between the state of visual-field functions and the morphology of the retina.

In addition, according to the present invention, it is possible to specify a new position related to a designated position, and find the layer thickness of the retina at this new position. Designation of a stimulation point in a visual-field examination enables measurement of the layer thickness of the retina at the new position related to this stimulation point (e.g. a position where a ganglion cell, which receives signals from a cone of this stimulation point, exists), so that it is possible to grasp the correspondence between the state of visual-field functions and the morphology of the retina.

BRIEF DESCRIPTION OF THE DRAWINGS

FIG. 8 is a table showing the relationship of the position and area of cone and ganglion cell.

FIG. 9A shows one example of the feature of scan of signal light when a fundus oculi is seen from the incident side of the signal light with respect to an eye. FIG. 9B shows one example of the feature of arrangement of scanning points on each scanning line.

PREFERRED EMBODIMENTS OF THE INVENTION

Figure 1:
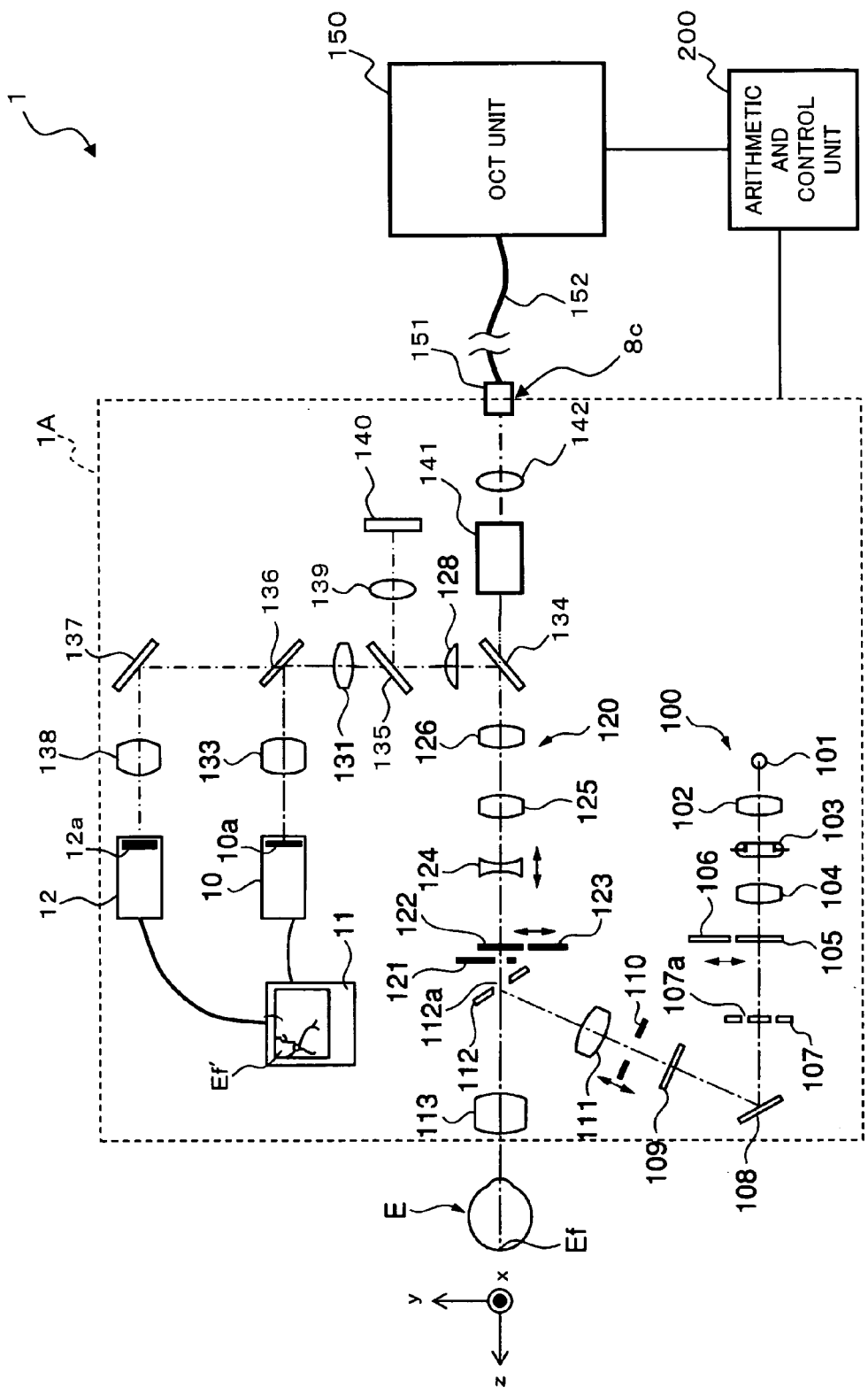
FIG. 1 is a schematic diagram showing one example of the entire configuration in an embodiment of the ophthalmologic examination apparatus according to the present invention.

An example of an embodiment of an ophthalmologic information-processing apparatus and an ophthalmologic examination apparatus according to the present invention will be explained in detail referring to the drawings.

The present invention evaluates the visual field of an eye based on an image (OCT image) obtained by an optical image measuring apparatus. Hereinafter, the ophthalmologic examination apparatus will be explained first along with an explanation of the OCT image.

Configuration of Ophthalmologic Examination Apparatus

Figure 2:
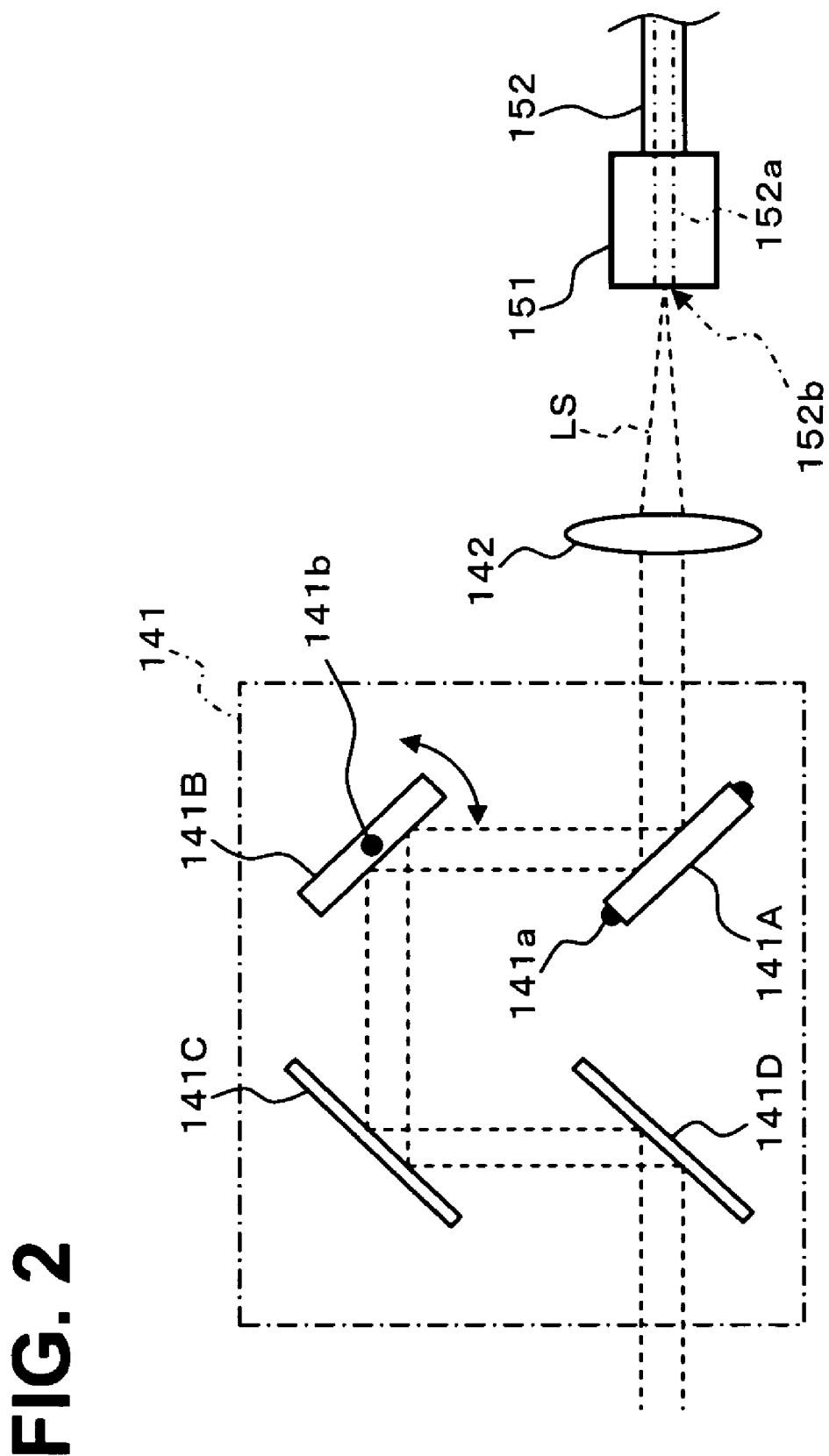
FIG. 2 is a schematic diagram showing one example of the configuration of a scanning unit in the embodiment of the ophthalmologic examination apparatus according to the present invention.
Figure 3:
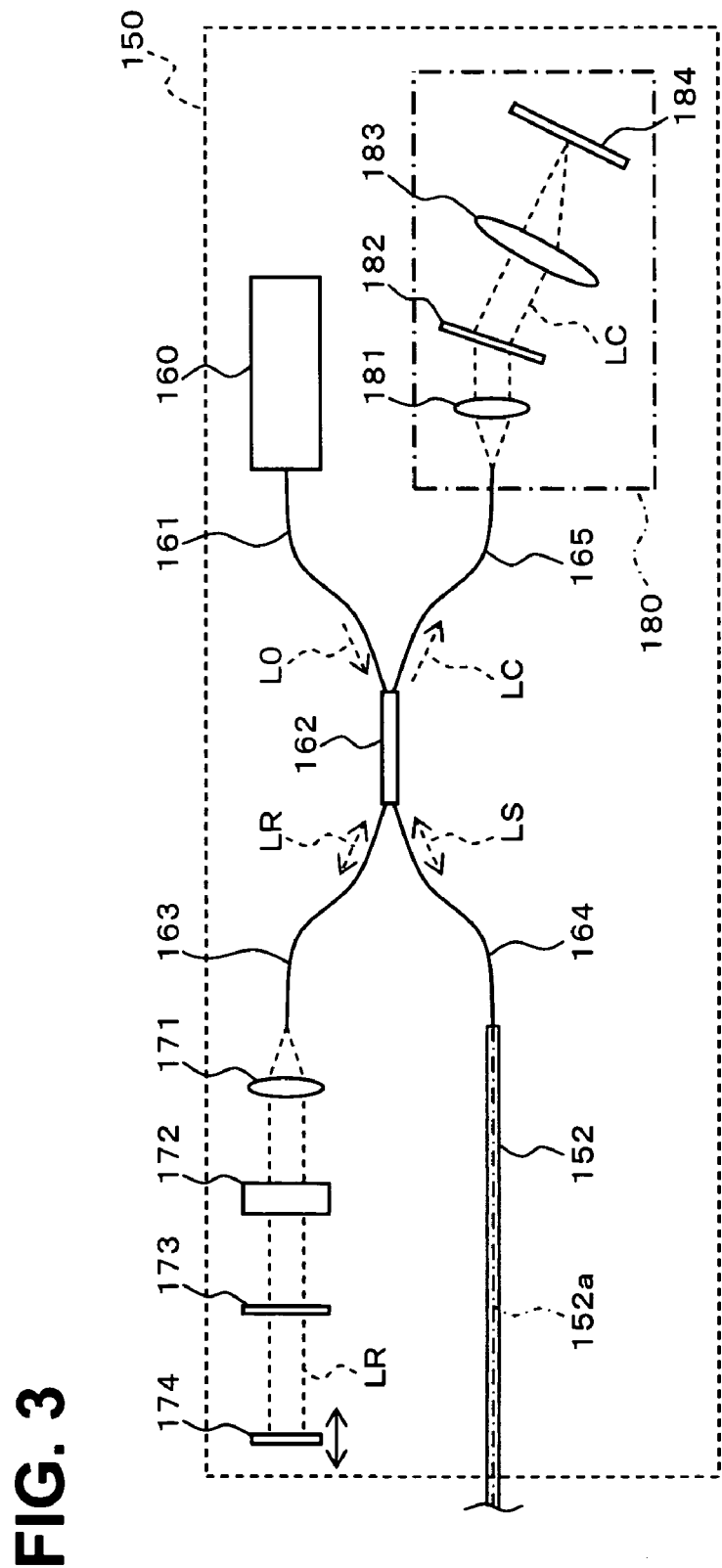
FIG. 3 is a schematic diagram showing one example of the configuration of an OCT unit in the embodiment of the ophthalmologic examination apparatus according to the present invention.
Figure 4:
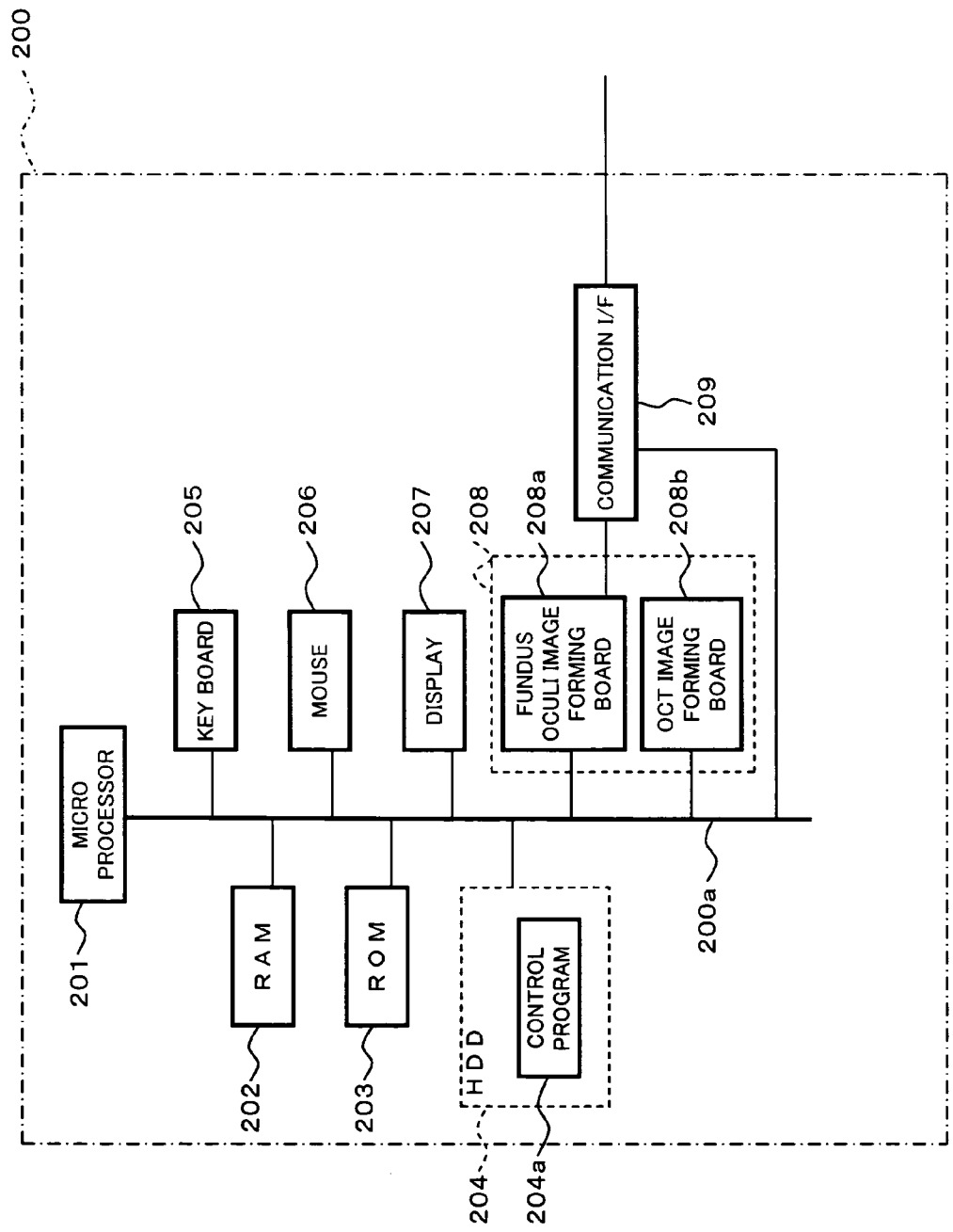
FIG. 4 is a schematic block diagram showing one example of the hardware configuration of an arithmetic and control unit in the embodiment of the ophthalmologic examination apparatus according to the present invention.
Figure 5:
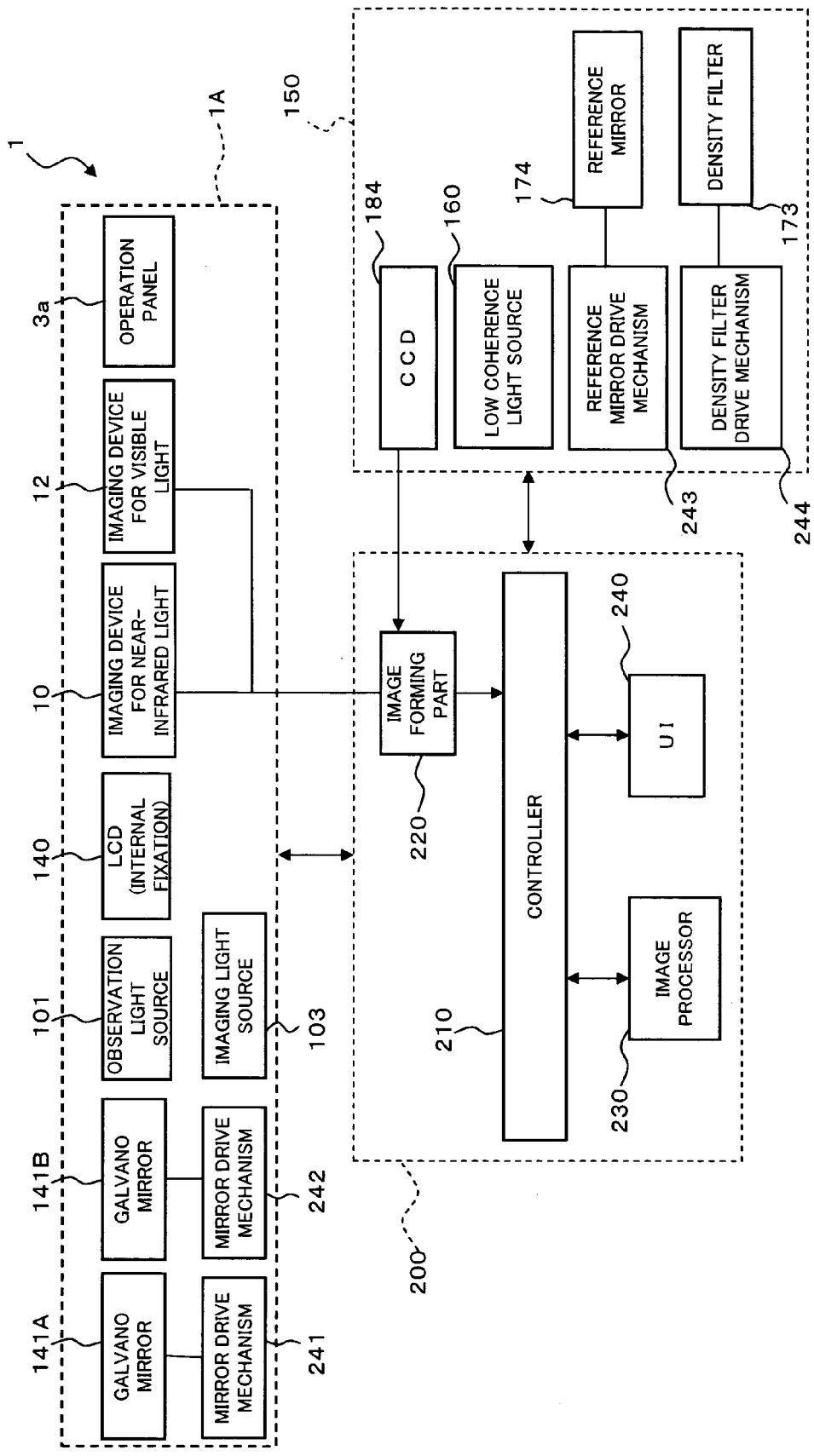
FIG. 5 is a schematic block diagram showing one example of the configuration of a control system in the embodiment of the ophthalmologic examination apparatus according to the present invention.
Figure 6:
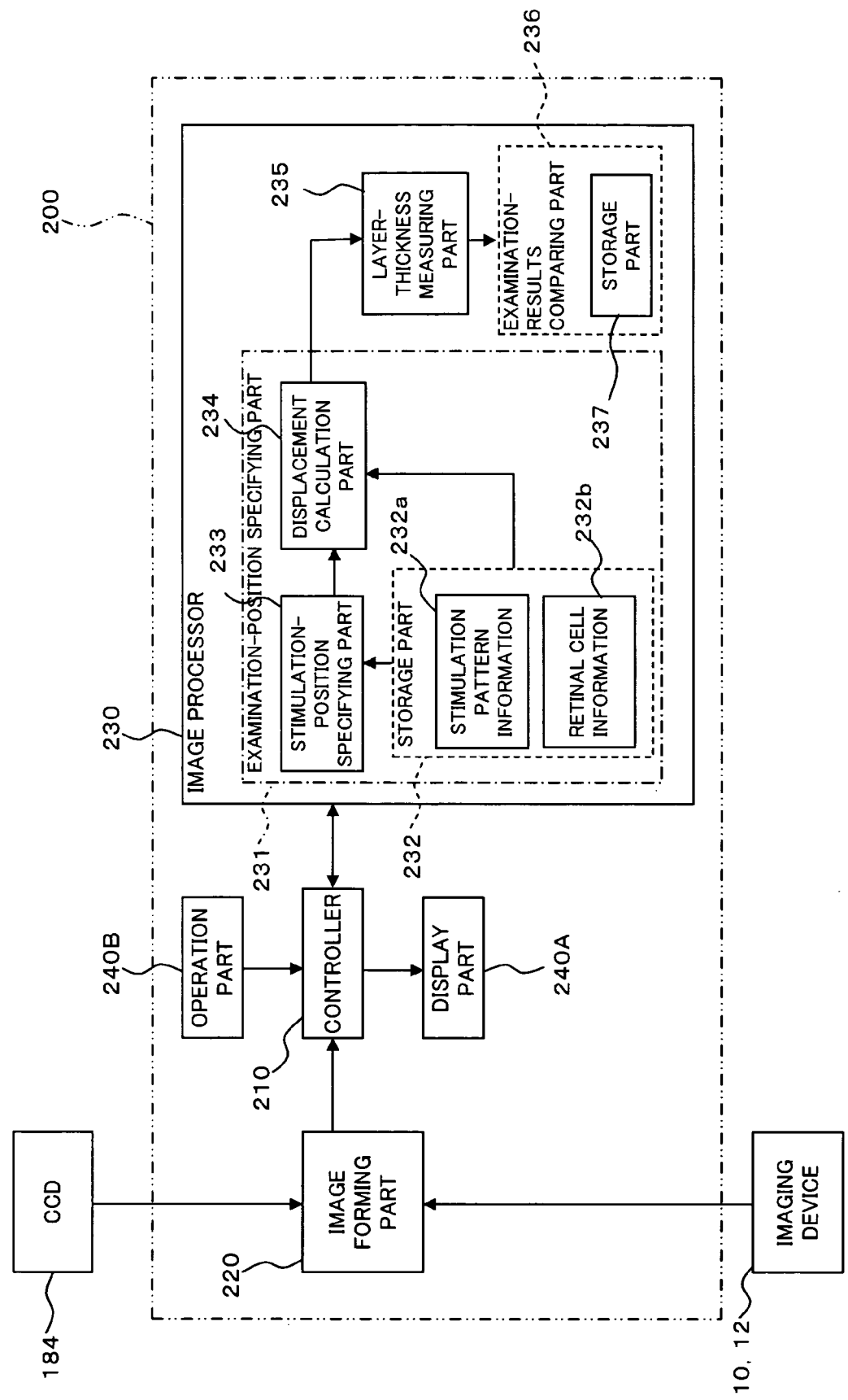
FIG. 6 is a schematic block diagram showing one example of the configuration of a control system in the embodiment of the ophthalmologic examination apparatus according to the present invention.

First, referring to FIGS. 1 through 6, the configuration of the ophthalmologic examination apparatus according to the present invention will be described. FIG. 1 shows the entire configuration of an ophthalmologic examination apparatus 1. FIG. 2 shows the configuration of a scanning unit 141 in a retinal camera unit 1A. FIG. 3 shows the configuration of an OCT unit 150. FIG. 4 shows the hardware configuration of an arithmetic and control unit 200. FIGS. 5 and 6 show the configuration of a control system of the ophthalmologic examination apparatus 1.

Entire Configuration

An ophthalmologic examination apparatus 1 comprises a retinal camera unit 1A, an OCT unit 150, and an arithmetic and control unit 200. The retinal camera unit 1A comprises an optical system similar to that of a conventional retinal camera used for imaging a 2-dimensional image of the surface of a fundus oculi. The OCT unit 150 houses an optical system that functions as an optical image measuring apparatus. The arithmetic and control unit 200 includes a computer executing various arithmetic processes, control processes, and the like.

To the OCT unit 150, one end of a connection line 152 is attached. To the other end of the connection line 152, a connector part 151 connecting the connection line 152 to the retinal camera unit 1A is attached. Inside the connection line 152, an optical fiber is installed conductively. Thus, the OCT unit 150 and the retina camera unit 1A are optically connected via the connection line 152.

Configuration of the Retinal Camera Unit

The retinal camera unit 1A is employed to image color images, monochrome images, or fluorescent images of the surface of a fundus oculi. Like a conventional retinal camera, the retinal camera unit 1A comprises an illumination optical system 100 and an imaging optical system 120.

The illumination optical system 100 comprises: an observation light source 101; a condenser lens 102; an imaging light source 103; a condenser lens 104; exciter filters 105 and 106; a ring transparent plate 107; a mirror 108; an LCD (liquid crystal display) 109; an illumination diaphragm 110; a relay lens 111; an aperture mirror 112; and an objective lens 113.

The observation light source 101 emits an illumination light having a wavelength of the visible region included within, for example, about 400 nm to 700 nm. The imaging light source 103 emits an illumination light having a wavelength in the near-infrared region included within, for example, about 700 nm to 800 nm. The near-infrared light emitted from this observation light source 103 is set so as to have a shorter wavelength than the light used by the OCT unit 150 (described later).

The imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; an imaging device 10 (image pick-up element 10a); a reflection mirror 137; an imaging lens 138; an imaging device 12 (image pick-up element 12a); a lens 139; and an LCD 140.

The dichroic mirror 134 reflects the fundus oculi reflection light (having a wavelength included within a range of about 400 nm to 800 nm) of the illumination light from the illumination optical system 100, and transmits a signal light LS (having a wavelength included within a range of, for example, about 800 nm to 900 nm; described later) from the OCT unit 150.

Further, the dichroic mirror 136 is configured to transmit the illumination light having a wavelength in the visible region, and to reflect the illumination light having a wavelength in the near-infrared region.

The LCD 140 displays a fixation target (internal fixation target) for fixing an eye E. The light from the LCD 140 is reflected by the half mirror 135 after being converged by the lens 139, and is reflected by the dichroic mirror 136 through the field lens 128. This light passes through the imaging lens 126, the relay lens 125, the variable magnifying lens 124, the aperture mirror 112 (aperture 112a thereof), the objective lens 113, etc. and enters the eye E. As a result, an internal fixation target is projected in a fundus oculi Ef.

The image pick-up element 10a is installed in the imaging device 10 such as a TV camera. The image pick-up element 10a is composed of a CCD (charge coupled device), a CMOS (complementary metal oxide semiconductor) or the like. The image pick-up element 10a detects light having a wavelength of the near-infrared region specifically. That is, the imaging device 10 is an infrared TV camera detecting near-infrared light. The imaging device 10 outputs a video signal as a result of detection of near-infrared light.

A touch panel monitor 11 displays a 2-dimensional image (fundus oculi image Ef) of the surface of the fundus oculi Ef, based on this video signal. This video signal is sent to the arithmetic and control unit 200, and the fundus oculi image is displayed on the display (described later). When the fundus oculi is imaged by the imaging device 10, the illumination light emitted from the imaging light source 103 and having a wavelength in the near-infrared region is used.

The image pick-up element 12a is an image pick-up element such as a CCD and a CMOS installed in the imaging device 12 such as a TV camera, and detects light of a wavelength in the visible region specifically. That is, the imaging device 12 is a TV camera detecting visible light. The imaging device 12 outputs a video signal as a result of detection of visible light.

The touch panel monitor 11 displays a 2-dimensional image (fundus oculi image Ef) of the surface of the fundus oculi Ef, based on this video signal. Further, this video signal is sent to the arithmetic and control unit 200, and the fundus oculi image Ef is displayed on a display (described later). At the time of fundus oculi imaging by the imaging device 12, the illumination light emitted from the observation light source 101 and having a wavelength in the visible region is used.

The retinal camera unit 1A is provided with a scanning unit 141 and a lens 142. The scanning unit 141 has a configuration for scanning a target position of light (signal light LS; described later) outputted from the OCT unit 150 to the fundus oculi Ef.

The lens 142 makes the signal light LS guided from the OCT unit 150 through the connection line 152 enter the scanning unit 141 in the form of a parallel light flux. Further, the lens 142 converges the fundus oculi reflection light of the signal light LS passed through the scanning unit 141.

One example of the configuration of the scanning unit 141 is shown in FIG. 2. The scanning unit 141 comprises Galvano mirrors 141A, 141B, and reflection mirrors 141C, 141D.

The Galvano mirrors 141A and 141B are reflection mirrors disposed so as to be rotatable about rotary shafts 141a and 141b, respectively. The Galvano mirrors 141A and 141B are rotated by mirror drive mechanisms 241 and 242, which will be described later (refer to FIG. 5), respectively. Consequently, the orientations of reflection surfaces (faces reflecting the signal light LS) of the Galvano mirrors 141A and 141B are changed, respectively.

The rotary shafts 141a and 141b are arranged perpendicular to each other. In FIG. 2, the rotary shaft 141a of the Galvano mirror 141A is arranged in a direction parallel to the paper face. Meanwhile, the rotary shaft 141b of the Galvano mirror 141B is arranged in a direction perpendicular to the paper face.

That is, the Galvano mirror 141B is rotatable in the directions indicated by an arrow pointing in both directions in FIG. 2, while the Galvano mirror 141A is rotatable in the directions perpendicular to the arrow pointing in both the directions. As a result, the Galvano mirrors 141A and 141B can change the reflecting directions of the signal light LS to directions perpendicular to each other. As can be seen from FIG. 1 and FIG. 2, the signal light LS is scanned in the x direction when the Galvano mirror 141A is rotated, and the signal light LS is scanned in the y direction when the Galvano mirror 141B is rotated.

The signal lights LS reflected by the Galvano mirrors 141A and 141B are reflected by reflection mirrors 141C and 141D, and advances in the same directions as having entered the Galvano mirror 141A.

An end face 152b of the optical fiber 152a inside the connection line 152 is arranged facing the lens 142. The signal light LS emitted from this end face 152b advances while expanding its beam diameter toward the lens 142, and is made to become a parallel light flux by the lens 142. On the contrary, the signal light LS passed through the fundus oculi Ef is converged toward the end face 152b by the lens 142, and enters the optical fiber 152a.

Configuration of OCT Unit

Next, the configuration of the OCT unit 150 will be described referring to FIG. 3. The OCT unit 150 has a configuration for forming a tomographic image of the fundus oculi Ef.

The OCT unit 150 comprises an optical system similar to that of a conventional optical image measuring apparatus. The OCT unit 150 splits low-coherence light into a reference light and a signal light, and generates and detects an interference light by superimposing the signal light passed through the fundus oculi and the reference light passed through the reference object. The results of this detection (detection signals) are inputted into the arithmetic and control unit 200. The arithmetic and control unit 200 forms a tomographic image of the fundus oculi (in particular, the retina) by analyzing these detection signals.

A low coherence light source 160 is composed of a broadband light source that emits low coherence light L0. As the low coherence light source 160, for example, a super luminescent diode (SLD) or a light emitting diode (LED) is used.

For example, this low coherence light L0 includes a light having a wavelength in the near-infrared region, and has a time-wise coherence length of approximately several tens of micrometers. Moreover, the low coherence light L0 has a longer wavelength than the illumination light (wavelength: about 400 nm to 800 nm) of the retinal camera unit 1A, for example, a wavelength included within about 800 nm to 900 nm.

The low coherence light L0 emitted from the low coherence light source 160 is guided to an optical coupler 162 through an optical fiber 161. The optical fiber 161 is composed of, e.g. a single mode fiber or a PM (Polarization maintaining) fiber. The optical coupler 162 splits the low coherence light L0 into reference light LR and signal light LS.

The optical coupler 162 acts as both a part for splitting light (splitter) and a part for superposing lights (coupler), but is referred to as an "optical coupler" idiomatically herein.

The reference light LR is guided by an optical fiber 163 and emitted from the end face of the fiber. The optical fiber 163 is composed of a single mode fiber or the like. Furthermore, the reference light LR is made to be a parallel light flux by a collimator lens 171, passed through a glass block 172 and a density filter 173, and reflected by a reference mirror 174.

The reference light LR reflected by the reference mirror 174 is again passed through the density filter 173 and the glass block 172, converged to the fiber end face of the optical fiber 163 by the collimator lens 171, and guided to the optical coupler 162 through the optical fiber 163.

Herein, the glass block 172 and the density filter 173 act as a delaying part for matching the light path lengths (optical distances) of the reference light LR and the signal light LS, and as a dispersion correction part for matching the dispersion characteristics of the reference light LR and the signal light LS.

The density filter 173 also acts as a dark filter for reducing the amount of the reference light, and is composed of a rotating ND (neutral density) filter, for example. The density filter 173 changes the reduction amount of the reference light LR by being rotary driven by a density filter drive mechanism 244 described later (refer to FIG. 5). That makes it possible to regulate the amount of the reference light LR contributing to generation of the interference light LC.

The reference mirror 174 can be moved in the traveling direction (the direction of the arrow pointing both sides shown in FIG. 3) of the reference light LR. As a result, it is possible to ensure a light path length of the reference light LR in accordance with an axial length of the eye E, a working distance (distance between the objective lens 113 and the eye E), and the like. Moreover, it is possible to obtain images at arbitrary depth positions of the fundus oculi Ef, by moving the reference mirror 174. The reference mirror 174 is moved by a reference mirror drive mechanism 243 described later (refer to FIG. 5).

The signal light LS generated by the optical coupler 162 is guided to the end of the connection line 152 through an optical fiber 164. The optical fiber 164 is composed of a single mode fiber or the like. The optical fiber 152a conductively runs inside the connection line 152. Herein, the optical fiber 164 and the optical fiber 152a may be composed of a single optical fiber, or may be jointly formed by connecting the end faces of the respective fibers.

The signal light LS is guided in the connection line 152, and is guided to the retinal camera unit 1A. Furthermore, the signal light LS is applied to the eye E through the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the light path in advance when the signal light LS is applied to the eye E.

The signal light LS having entered the eye E forms an image on the fundus oculi Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef contains information reflecting the morphology of the surface of the fundus oculi Ef and information reflecting the state of backscattering at the refractive index boundary of the deep area tissue of the fundus oculi Ef. This light may be simply referred to as "fundus oculi reflection light of the signal light LS.

The fundus oculi reflection light of the signal light LS advances reversely on the above path within the retinal camera unit 1A to be converged at the end face 152b of the optical fiber 152a, enters into the OCT unit 150 through the optical fiber 152a, and returns to the optical coupler 162 through the optical fiber 164.

The optical coupler 162 superimposes the signal light LS returning through the eye E on the reference light LR reflected at the reference mirror 174, thereby generating the interference light LC. The interference light LC is guided into a spectrometer 180 through an optical fiber 165. The optical fiber 165 is composed of a single mode fiber or the like.

In the present embodiment, a Michelson-type interferometer is used, but it is possible to use any type of interferometer such as a Mach Zender type.

The spectrometer 180 comprises a collimator lens 181, a diffraction grating 182, an image forming lens 183, and a CCD 184. The diffraction grating 182 may be a transmission-type diffraction grating that transmits light, or may be a reflection-type diffraction grating that reflects light. Further, it is also possible to use, in place of the CCD 184, other photo-detecting elements such as CMOS.

The interference light LC having entered the spectrometer 180 is split (resolved into spectra) by the diffraction grating 182 after converged into a parallel light flux by the collimator lens 181. The split interference light LC forms an image on a detecting surface of the CCD 184 by the image forming lens 183. The CCD 184 detects each spectrum of the interference light LC to convert into a electric signal, and outputs the detection signal to the arithmetic and control unit 200.

Configuration of Arithmetic and Control Unit

The configuration of the arithmetic and control unit 200 will be described. The arithmetic and control unit 200 analyzes the detection signal inputted from the CCD 184 of the OCT unit 150, and forms a tomographic image of the fundus oculi Ef. A technique for this analysis is the same technique as a conventional technique for the Fourier domain OCT.

Further, the arithmetic and control unit 200 forms a 2-dimensional image showing the morphology of the surface of the fundus oculi Ef, based on the video signals outputted from the imaging devices 10 and 12 of the retinal camera unit 1A.

Furthermore, the arithmetic and control unit 200 controls each part of the retinal camera unit 1A and OCT unit 150.

The control of the retinal camera unit 1A is, for example: control of the observation light source 101 and the imaging light source 103; control of insertion/retraction operation of the exciter filters 105 and 106 and the barrier filters 122 and 123 to/from the light path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic and control unit 200 executes control of the operation of the Galvano mirrors 141A and 141B.

Further, the control of the OCT unit 150 is, for example: control of the low coherence light source 160; control of shift of the reference mirror 174; control of the rotary operation of the density filter 173 (operation of changing the reduction amount of the reference light LR); and control of the accumulated time of the CCD 184.

The hardware configuration of the arithmetic and control unit 200 as described above will be described referring to FIG. 4.

The arithmetic and control unit 200 is provided with a hardware configuration similar to that of a conventional computer. To be specific, the arithmetic and control unit 200 comprises: a microprocessor 201, a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 comprises a CPU (central processing unit), an MPU (micro processing unit), or the like. The microprocessor 201 executes operations characteristic to the present embodiment, by loading a control program 204a stored in the hard disk drive 204, onto the RAM 202.

The microprocessor 201 executes control of each part of the apparatus described above, various arithmetic processes, etc. Moreover, the microprocessor 201 receives an operation signal from the keyboard 205 or the mouse 206, and controls each part of the apparatus corresponding to the operation signal. Furthermore, the microprocessor 201 executes control of a display process by the display 207, control of a process of transmitting/receiving various data and signals by the communication interface 209, and so on.

The keyboard 205, the mouse 206 and the display 207 are used as user interfaces in the ophthalmologic examination apparatus 1. The keyboard 205 is used as, for example, a device for typing letters, figures, etc. The mouse 206 is used as a device for performing various input operations to the display screen of the display 207.

Further, the display 207 is a display device such as an LCD and a CRT (Cathode Ray Tube) display. The display 207 displays various images such as images of the fundus oculi Ef formed by the ophthalmologic examination apparatus 1, and displays various screens such as an operation screen and a set-up screen.

The user interface of the ophthalmologic examination apparatus 1 is not limited to the above configuration, and may include, e.g., a track ball, a control lever, a touch panel type of LCD, and a control panel for ophthalmology examinations. As the user interface, it is possible to employ any configuration equipped with a function to display and output information, and a function to input information and operate the apparatus.

The image forming board 208 is a dedicated electronic circuit for forming (image data of) an image of the fundus oculi Ef. This image forming board 208 is provided with a fundus oculi image forming board 208a and an OCT image forming board 208b.

The fundus oculi image forming board 208a is a dedicated electronic circuit that forms image data of fundus oculi images, based on the video signals from the imaging device 10 and the imaging device 12.

Further, the OCT image forming board 208b is a dedicated electronic circuit that forms image data of tomographic images of the fundus oculi Ef, based on the detection signals from the CCD 184 of the OCT unit 150.

By providing the image forming board 208, it is possible to increase the processing speed for forming fundus oculi images and tomographic images.

The communication interface 209 sends the control signal from the microprocessor 201, to the retinal camera unit 1A or the OCT unit 150. Moreover, the communication interface 209 receives the video signals from the imaging devices 10 and 12 and the detection signal from the CCD 184 of the OCT unit 150, and inputs the signals to the image forming board 208. At this time, the communication interface 209 operates to input the video signals from the imaging devices 10 and 12, to the fundus oculi image forming board 208a, and input the detection signal from the CCD 184, to the OCT image forming board 208b.

In a case where the arithmetic and control unit 200 is in a condition connectable to a communication network such as a LAN (Local Area Network) and the Internet, the communication interface 209 may be equipped with a network adapter like a LAN card or communication equipment like a modem. In this case, by installing a server accommodating the control program 204a on the communication network, and at the same time, configuring the arithmetic and control unit 200 as a client terminal of the server, it is possible to make the ophthalmologic examination apparatus 1 operate.

Configuration of Control System

Next, the configuration of the control system of the ophthalmologic examination apparatus 1 will be described referring to FIGS. 5 and 6.

Controller

The control system of the ophthalmologic examination apparatus 1 is configured mainly having a controller 210 of the arithmetic and control unit 200. The controller 210 comprises the microprocessor 201, the RAM202, the ROM203, the hard disk drive 204 (control program 204a), the communication interface 209, and so on. The controller 210 executes the aforementioned various controls.

Image Forming Part

An image forming part 220 forms image data of the fundus oculi image Ef based on the video signals from the imaging devices 10 and 12. Moreover, the image forming part 220 forms image data of the tomographic images of the fundus oculi Ef based on the detection signals from the CCD 184 of the OCT unit 150.

The imaging forming part 220 comprises the image forming board 208 and the communication interface 209. In this specification, "image data" and "image" presented thereby may be identified with each other.

Image Processor

The image processor 230 executes various image processing and analysis processing based on image data of images formed by the image forming part 220. For example, the image processing part 230 executes various correction processes such as brightness correction and dispersion correction of the images.

In addition, the image processor 230 forms a 3-dimensional image of the fundus oculi Ef by applying interpolation processes for interpolating pixels between tomographic images, to tomographic images formed by the image forming part 220.

Incidentally, a 3-dimensional image refers to an image that is defined by using a 3-dimensional coordinate system. In other words, a 3-dimensional image means an image in which pixels are arranged 3-dimensionally.

One example of a 3-dimensional image is an image that is obtained by arranging a plurality of tomographic images in a 3-dimensional space; that is, an image that is obtained by embedding a plurality of tomographic images into a 3-dimensional space in accordance with the positional relationships thereof. Image data of such an image is referred to as stack data or the like.

Further, a 3-dimensional image may be an image defined by voxels, which are 3-dimensional pixels. Image data of such an image is referred to as volume data, voxel data, or the like. When displaying an image based on volume data, the image processor 230 applies a rendering process to this volume data, and forms image data of a pseudo 3-dimensional image seen from a specified viewing direction. Herein, the rendering process is, for example, volume rendering and MIP (Maximum Intensity Projection).

Examination-Position Specifying Part

The image processor 230 is provided with an examination-position specifying part 231. The examination-position specifying part 231 specifies, in a 3-dimensional image, a position corresponding to a stimulation point in a visual-field examination. The examination-position specifying part 231 is an example of the "specifying part" according to the present invention. Hereinafter, the configuration and operation of the examination-position specifying part 231 will be explained.

The examination-position specifying part 231 is provided with storage 232, a stimulation-position specifying part 233, and a displacement calculation part 234.

Storage

The storage 232 stores information that is referred to by the stimulation-position specifying part 233 or the displacement calculation part 234. Stimulation pattern information 232a is stored as the information referred to by the stimulation-position specifying part 233. Retinal cell information 232b is stored as the information referred to by the displacement calculation part 234.

The stimulation pattern information 232a will now be explained. As a preparation for that, the examination of a visual field is briefly explained first. In the examination of a visual field (static examination of a visual field), the sensitivity threshold at each stimulation point is obtained by projecting a spotlight toward the stimulation points on the retina. The spotlight is generally projected toward a plurality of stimulation points. The plurality of stimulation points are arranged in a pattern according to the state of the eye and the contents of the examination (e.g. cf. Japanese Unexamined Patent Application Publication 2003-235800).

Figure 7:
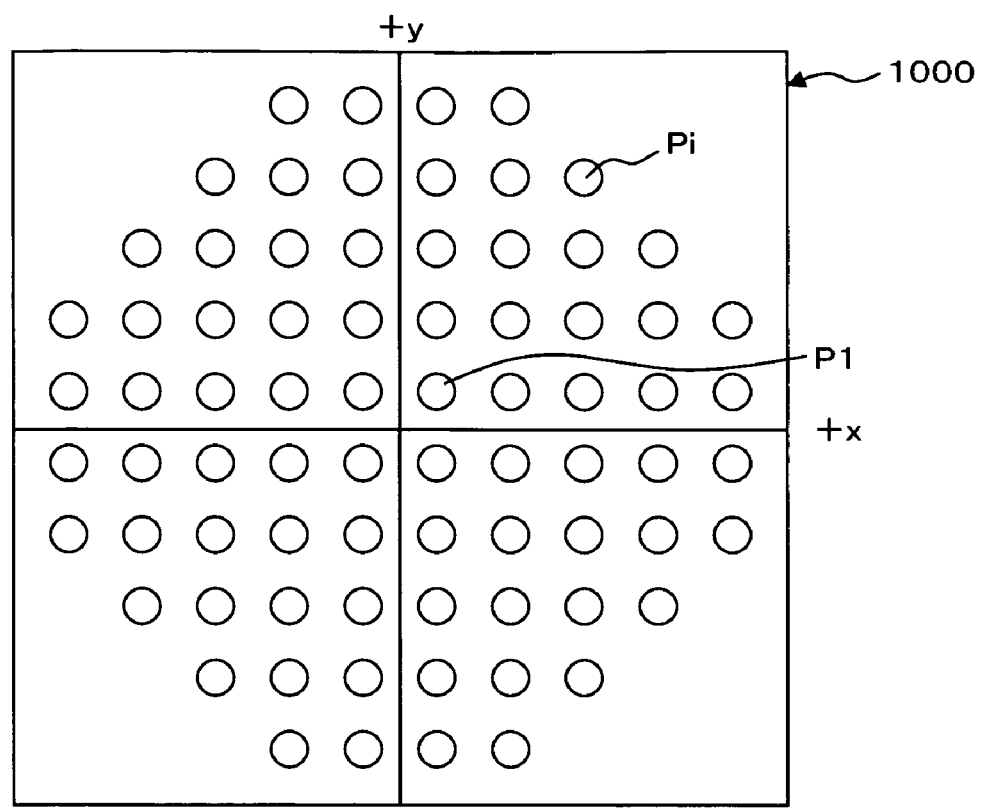
FIG. 7 is a schematic diagram showing one example of an arrangement pattern of stimulation points of the retina in a visual-field examination.

An example of the arrangement pattern of the stimulation points (stimulation pattern) is shown in FIG. 7. A stimulation pattern 1000 represents an arrangement of a plurality of stimulation points Pi (i=1 through 76). The stimulation points Pi are arranged 2-dimensionally at intervals of two degrees within a ten-degree range of the view angle. In the examination, the eye is fixed so that the central position of the stimulation pattern 1000 (the point of intersection of the vertical line and the horizontal line in FIG. 7) is located at the fovea centralis (preferably, the central pit).

Incidentally, the stimulation pattern is not limited to that shown in FIG. 7. For example, it is possible to apply a stimulation pattern in which stimulation points are arranged within a range of an arbitrary view angle. In addition, it is also possible to apply a stimulation pattern in which an arbitrary number of stimulation points are arranged, or a stimulation pattern in which stimulation points are arranged in an arbitrary pattern.

The stimulation pattern information 232a records such a stimulation pattern. The stimulation pattern information 232a may be a template image of a stimulation pattern, or may be the coordinate values of each stimulation point (e.g. coordinate values using the central position as the origin). Whatever the case, the stimulation pattern information 232a only needs to be information that represents an arrangement of stimulation points indicated in the stimulation pattern.

The retinal cell information 232b is explained. As a preparation for that, structure of retina is briefly explained. The retina has, in order from the surface of the fundus oculi toward the deer side, inner limiting membrane, a nerve fiber layer, a ganglionic cell layer, an inner plexiform layer, an inner nuclear layer, an outer plexiform layer, an outer nuclear layer, an outer limiting membrane, a neuroepitheliale layer, and a retinal pigment epithelium (which may vary depending on the site).

In addition, cells composing the retina include photoreceptor cells (cone and rod), bipolar cells, horizontal cells, amacrine cells, and ganglion cells (e.g. cf. Japanese Unexamined Patent Application Publication 2004-121707). The photoreceptor cells sense light and convert it into nerve signals. These nerve signals are transmitted to the bipolar cells and horizontal cells. The bipolar cells are synaptic-connected to the amacrine cells and the ganglion cells. The nerve signals are transmitted to the visual center of the cerebrum via the axon of the ganglion cells and visual nerves.

The photoreceptor cells are located in the neuroepitheliale layer, and the ganglion cells are located in the ganglion cell layer in the proximity of the surface of the fundus oculi. In other words, photoreceptor cells and ganglion cells are different from each other in terms of their depth positions (z-coordinate values).

In addition, for the photoreceptor cells and the ganglion cells that are coupled to each other, it is known that their positions in the lateral direction (position in the x-y coordinate plane) are different from each other. In recent years, studies regarding the displacement between the photoreceptor cell and the ganglion cells have been advanced.

Those study results are disclosed, for example, in the paper by Johann Sjostrand et al. entitled "Morphometric Study of the displacement of retinal ganglion cells subserving cones within the human fovea," published in Graefe's archive for clinical and experimental ophthalmology, Springer Berlin/Heidelberg, Vol. 237, Number 12 December, 1999.

This research paper describes that a displacement A of the cones and displacement B of the ganglion cells to the fovea centralis (central pit) have the following relationship:

$$B = 1.29 \cdot (A + 0.046)^{0.67} \tag{1}$$

This research paper also describes, for the displacement of the cones, the total displacement, the displacement of the ganglion cells, and the area ratio of the cones and the ganglion cells, the relationships indicated in the table T in FIG. 8.

Incidentally, in the table T, "deg" refers to the view angle. In addition, $A_C$ refers to the area of the cones, and $A_{RGC}$ refers to the area of the ganglion cells.

Moreover, the displacement of the ganglion cells is represented by the sum of the displacement of the cones and the total displacement. Incidentally, the total displacement is the sum of the displacement of the Henle's fiber layer and the displacement of the bipolar cell.

The retinal cell information 232b includes information that is based on the table T. This information may be taken directly from the table T itself, or may be information that is created based on the table T. As an example of the latter, there is information that is obtained by interpolating data indicated in the table T by means of an arbitrary statistical technique. Incidentally, when the retinal cell information 232b includes the table T itself, the displacement calculation part 234 can execute similar data interpolations.

The retinal cell information 232b needs to include only information that associates the position of the cone and the position of the ganglion cell (association information). Herein, the position of the cone or the ganglion cell is defined as the displacement from the fovea centralis. In other words, a stimulation point in an visual-field examination is defined as a position relative to the fixed position (ideally, the central pit), and a light to be projected onto each stimulation point stimulates the cone, so that the position of the ganglion cell to be associated with a certain stimulation point (cone) represents the position of the ganglion cell that receives nerve signals from the cone.

In addition, the retinal cell information 232b includes data of the area ratio indicated in the table T. Furthermore, the retinal cell information 232b includes the above formula (1).

Information included in the retinal cell information 232b does not need to be information that is based on the data described in the abovementioned research paper. For example, the retinal cell information 232b may include data that is based on other study results, or may include data that is based on the analysis result of clinical data obtained in advance.

Stimulation-Position Specifying Part

The stimulation-position specifying part 233 specifies, in a 3-dimensional image, a position corresponding to each stimulation point that is included in the stimulation pattern indicated in the stimulation pattern information 232a. Incidentally, when two or more stimulation patterns are recorded in the stimulation pattern information 232a, the stimulation-position specifying part 233 specifies the position in the 3-dimensional image based on a stimulation pattern that has been selected either automatically or manually.

A specific example of the processes executed by the stimulation-position specifying part 233 is explained. First, a reference position in the 3-dimensional image is specified. The reference position is, for example, the fovea centralis (central pit) of the surface of the fundus oculi. Incidentally, when a visual-field examination has already been implemented for the eye E in the past and the fixed position used at that time has been recorded, this fixed position can be the reference position. In addition, in cases in which certain propensities when fixing the eye E (a tendency of fixation misalignment) is known, the reference position can be decided by reflecting this propensity.

The process of specifying the reference position is performed by analyzing the pixel values or voxel values of the 3-dimensional image. The stimulation-position specifying part 233 first obtains an image region equivalent to the surface of the fundus oculi from the 3-dimensional image. This process may be extraction of the image region from the 3-dimensional image, or may be creation of a pseudo 2-dimensional image (accumulated image) of the surface of the fundus oculi that is obtained by accumulating the 3-dimensional images in the depth direction. Incidentally, the accumulated image is disclosed in Japanese Unexamined Patent Application Publication 2007-130403.

Next, pixels in this image are analyzed to specify the reference position. For example, when the fovea centralis is the reference position, by utilizing the fact that macular area is expressed more darkly than other sites in a fundus oculi image (i.e. the brightness value is small), a region where the brightness value is smaller than a predetermined threshold (region equivalent to macular area) is specified. This threshold may be decided statistically, for example, using clinical data, or may be decided by creating a histogram of the brightness value of each pixel in the image region. After specification of the region where the brightness value is smaller than the threshold, this region is approximated with an ellipse, and the center of this approximate ellipse (intersection of the long axis and the short axis) is found. This center position is employed as the reference position.

Another example of the process of specifying the reference position is explained. First, as is the case with the above example, an image region equivalent to the surface of the fundus oculi is obtained. Next, a 3-dimensional shape of the image region is found. Then, a depression equivalent to the macular area is specified based on this 3-dimensional shape, and the deepest part of this depression is designated as the reference position.

After specification of the reference position in the 3-dimensional image, a position in the 3-dimensional image corresponding to each stimulation point is specified based on this reference position and the stimulation pattern. In this process, first, the central position of the stimulation pattern (described above) is matched with the reference position. At this time, the size of the stimulation pattern is adjusted depending on the magnification ratio (field angle) of the 3-dimensional image. Next, in the stimulation pattern in which the central position is matched with the reference position, a position in the 3-dimensional image overlapping each stimulation point (stimulation position) is specified.

Displacement Calculation Part

The displacement calculation part 234 specifies, based on the retinal cell information 232$b$ (cf. the table T in FIG. 8), a position related to the stimulation position that has been specified by the stimulation-position specifying part 233 (related position). The related position is, for example, a position where the ganglion cell, which receives signals from the cone existing at the stimulation position, exists.

A specific example of the process executed by the displacement calculation part 234 is explained. First, a 2-dimensional coordinate system is set in the stimulation pattern 1000 shown in FIG. 7. The central position of the stimulation pattern 1000 shall be the origin (0, 0) of the coordinate system. In addition, in the stimulation pattern 1000, the horizontal line shall be the x-coordinate axis (left hand is the +x direction) and the vertical axis shall be the y-coordinate axis (upside is the +y direction). Moreover, a view angle of one degree shall be equivalent to 0.3 mm, and the diameter of each stimulation point Pi shall be 0.13 mm.

Herein, a related position of the stimulation point P1, which is located at the immediate upper right of the center position, will be found. The coordinate of the stimulation point P1 is (x, y)=(0.3, 0.3). The distance from the central position to the stimulation point P1 is approximately 0.424 mm, as calculated using the Pythagorean theorem. This distance is the displacement, from the central position, of the cone that exists at the position of the stimulation point P1.

The displacement of the ganglion cell receiving signals from this cone, with respect to the central position can be calculated by employing the above formula (1).

Furthermore, the displacement of the ganglion cell with respect to the cone can be found by subtracting the displacement of the cone from the displacement of the ganglion cell. The adequacy of the calculation results can be verified referring to the table T. For example, according to the second line in the table T, the displacement of the cone (0.50 mm) and the displacement of the ganglion cell (0.86 mm) are made to correspond to each other, and the total displacement at that time is 0.36 mm. Therefore, the displacement of the cone at the stimulation point P1 (0.424 mm) is equivalent to the displacement of the ganglion cell (0.778 mm) (by interpolation processing or the like of the table T), so that the total displacement that is the difference between them is 0.354 mm. This value is almost equal to the above displacement value of 0.36 mm. The position of the ganglion cell that has been found in this way is represented by coordinate values of the x-y coordinate system, whereby the specifying processes of the position of the ganglion cell (i.e. the specifying processes of the related position of the stimulation point P1) are completed.

Next, the size of the region of this ganglion cell is found. In this process, the section of the "area ratio" in the table T is referred to. At this time, the relationship between the displacement of the cone and the area ratio is found based on the table T using, for example, linear approximation. Consequently, as the area ratio corresponding to the displacement of the cone 0.424 mm, a value 0.538 is obtained.

Taking the above into consideration, the area of the region of the ganglion cell can be found by the formula $\{\pi \times (0.13 \text{ mm}/2)^2\}/0.538$. Based on the arithmetic results, the diameter of the region can be found easily.

In the manner described above, the displacement calculation part 234 finds a related position for each stimulation point Pi and further sets an image region that includes each related position (the region of the ganglion cell described above).

Layer-Thickness Measuring Part

The layer-thickness measuring part 235 arithmetically calculates, by analyzing a 3-dimensional image of the retina, the layer thickness of the retina at the stimulation position or the related position that have been specified by the examination-position specifying part 231. Herein, the layer thickness of the retina may be the thickness of an arbitrary layer from the abovementioned layers of the retina, or may be the thickness of a region including two or more arbitrary layers. The layer-thickness measuring part 235 is an example of the "analyzing part" of the present invention.

An arithmetic technique for calculating the thickness of a layer is disclosed, for example, in Japanese Unexamined Patent Application Publication 2007-130403. Briefly explained, two or more predetermined layers (or boundary between layers) are first specified by analyzing a 3-dimensional image or a tomographic image, and then the distance between the specified layers is arithmetically calculated, thereby enabling the thickness of the layer to be found.

The layer-thickness measuring part 235 finds, for example, the layer thickness at two or more positions in an image region that includes the stimulation position (image region equivalent to the stimulation point Pi). The layer-thickness measuring part 235 can find the layer thickness at the stimulation position by statistically processing values of thickness of the two or more layers. Examples of this statistical process include a process for arithmetically calculating an average value. Incidentally, it is also possible to directly find the layer thickness of the stimulation position, but in this embodiment, the layer thickness of a stimulation position is found based on the layer thickness at various positions in proximity to the stimulation position, in order to improve the accuracy.

Examination-Results Comparing Part

An examination-results comparing part 236 compares the layer thickness of the retina that has been found by the layer-thickness measuring part 235 and the examination results of the visual-field examination. The examination-results comparing part 236 is an example of the "comparing part" of the present invention.

The examination-results comparing part 236 is configured to include storage 237 for storing examination results of a visual-field examination for the eye E. The examination results may be results of an examination that has been implemented before an image is obtained by the ophthalmologic examination apparatus 1, or may be those of an examination that has been implemented after obtaining the image.

The visual-field examination is implemented with a perimeter that is different from that of the ophthalmologic examination apparatus 1. The perimeter directly transmits examination results to the ophthalmologic examination apparatus 1 via, for example, a communication line such as a LAN. Alternatively, it may be adapted to transmit examination results from the perimeter to a database on the communication line and to read, using the ophthalmologic examination apparatus 1, the examination results kept in the database. In these cases, the controller 210 (communication interface 209) acts as the "accepting part" for accepting examination results.

Alternatively, it may also be adapted to record examination results that have been obtained by the perimeter in a recording medium (such as a DVD-ROM) and to read the examination results from the recording medium using a drive apparatus (not shown in the drawings) mounted on the ophthalmologic examination apparatus 1. In this case, the drive apparatus acts as the "accepting part."

The examination results that have been accepted as above are stored in the storage 237 by the controller 210. In addition, the storage 237 stores in advance standard value information that represents the standard values of the layer thickness of a retina. The standard value information is statistically created based on, for example, clinical data, and represents normal ranges of the layer thickness of a retina. This normal range is decided based on, for example, the average values or standard deviations of the clinical data. The standard value information is created, for example, per stimulation pattern, and represents a normal range of the layer thickness at each stimulation point.

Sensitivity thresholds at a plurality of stimulation points are recorded in the examination results of a visual-field examination. Herein, in this visual-field examination, the stimulation pattern 1000 in FIG. 7 shall be used. At this time, it is desirable that the stimulation pattern to be used in the visual-field examination and the stimulation pattern in which a stimulation position is specified by the examination-position specifying part 231 are identical. When the stimulation pattern used in the examination of visual field is known, such as when examination results are stored previously, it is possible to configure the stimulation-position specifying part 233 to select this stimulation pattern from the stimulation pattern information 232*a* and to employ the same. In general, it is sufficient if at least one stimulation point at an identical position is included. In this case, the stimulation point at the identical position is to be compared.

As described above, for each stimulation position in the 3-dimensional image, the normal range for the layer thickness at the corresponding stimulation point is recorded in the standard value information. The examination-results comparing part 236 determines whether the layer thickness at each stimulation position is within the normal range for the corresponding stimulation point. When it is within the normal range, the layer thickness at the stimulation position (stimulation point) is determined to be appropriate, but when it is not, it is determined to be inappropriate.

In addition, the examination-results comparing part 236 obtains the sensitivity threshold at each stimulation point from the examination results of the visual-field examination. In this case, the normal ranges for the sensitivity threshold is previously stored in the storage 237, and the examination-results comparing part 236 determines whether the sensitivity threshold at each stimulation point is within the normal range. When it is within the normal range, the layer thickness at the stimulation position (stimulation point) is determined to be appropriate, but when it is not, it is determined to be inappropriate. Incidentally, when the adequacy of the sensitivity threshold at each stimulation point has already been included in the examination results of the visual-field examination, such a process need not be performed.

Furthermore, the examination-results comparing part 236 compares, for each stimulation point (stimulation position), the adequacy of the layer thickness, and the adequacy of the examination results. When both are appropriate, the state of the cone and the light detection function at the stimulation point is determined to be appropriate. Meanwhile, when both are inappropriate, the state of the cone and the light detection function at the stimulation point are determined to be inappropriate.

In addition, when the layer thickness is appropriate and the examination result is inappropriate, it is assumed that the light-detection function at the stimulation point has deteriorated due to causes other than the morphology of the retina. Moreover, when the layer thickness is inappropriate and the examination result is appropriate, it is assumed that the morphological deterioration of the retina has not progressed to an extent that would have an influence on the light-detection function, or that fixation misalignment has occurred in the visual-field examination.

Upon receiving such comparison results, the controller 210 generates a message for output. This message may be decided in advance by a combination of the adequacy of the layer thickness and the adequacy of the examination results.

The examination-results comparing part 236 can also perform a process similar to that performed for the above stimulation position for the layer thickness at a related position for each stimulation position. At this time, the standard value information stored in the storage 237 includes the standard values (normal range) of the layer thickness at each related position. Furthermore, it is also possible to generate, in a similar way, a message that represents the adequacy at the related position.

In addition, it is also possible to compare the adequacy at a stimulation position and the adequacy at a related position. For example, when both are appropriate, it can be determined that signals from the cone at the stimulation position are outputted from the ganglion cell at the related position to the brain. When both are inappropriate, it can be determined that there is a problem in both the cone and the ganglion cell. In addition, when the stimulation position is appropriate and the related position is inappropriate, it can be determined that the ganglion cell cannot appropriately relay signals that have been appropriately outputted from the cone. Moreover, when the stimulation position is inappropriate and the related position is appropriate, it can be determined that signals are not being inputted appropriately from the cone into the normal ganglion cell.

In addition, it is also possible to compare the adequacy at a related position and the examination results of a visual-field examination. Moreover, it is also possible to compare the adequacy at a stimulation position, the adequacy at a related position, and examination results of a visual-field examination.

The image processor 230 that operates as described above comprises the microprocessor 201, the RAM 202, the ROM 203, and the hard disk drive 204 (control program 204*a*).

User Interface

The user interface (UI) 240 comprises a display part 240A and an operation part 240B. The display part 240A is composed of a display device such as the display 207. The display part 240A specifically displays a message of the comparison results generated by the controller 210. The display part 240A is one example of the "output part" according to the present invention. Incidentally, an output part may be, for example, a printer for printing out, or may be an amplifier and speaker for voice output, other than the display device.

Further, the operation part 240B comprises an input device and an operation device such as the keyboard 205 and the mouse 206.

Signal Light Scanning and Image Processing

Scanning of the signal light LS is performed by the Galvano mirrors 141A and 141B of the scanning unit 141, as described above. The controller 210 controls the mirror drive mechanisms 241 and 242, respectively, to change the facing directions of the reflection surfaces of the Galvano mirrors 141A and 141B, thereby scanning the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling the two Galvano mirrors 141A and 141B, it is possible to scan the signal light LS in any direction on the x-y plane.

Figure 9A:
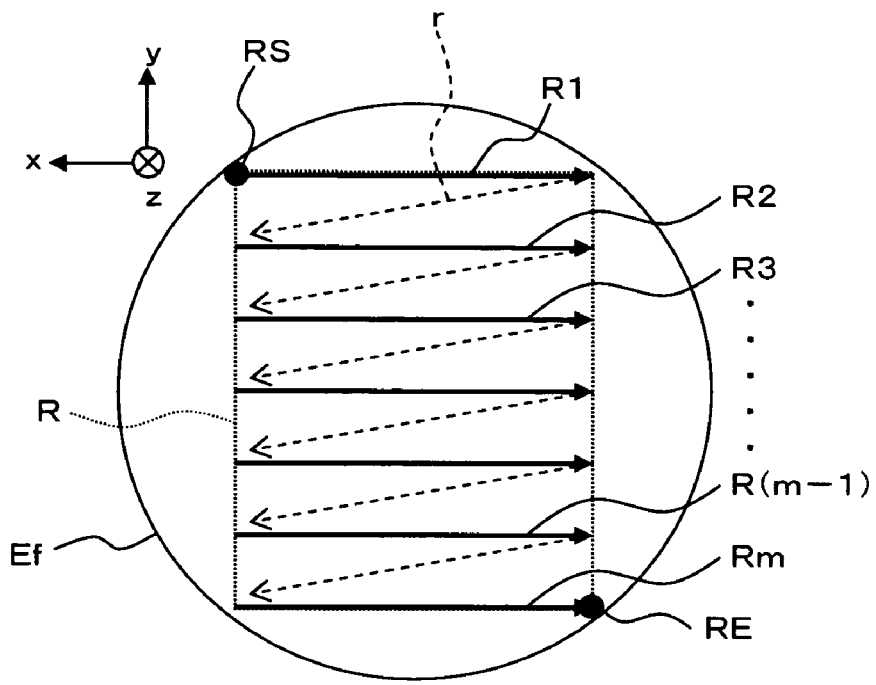
FIGS. 9A and 9B are schematic diagrams showing one example of the feature of scan of signal light in the embodiment of the ophthalmologic examination apparatus according to the present invention.
Figure 9B:
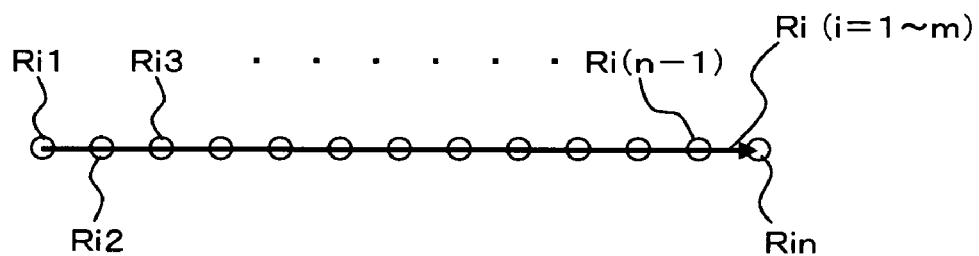

FIGS. 9A and 9B show one example of the feature of scanning of the signal light LS for forming images of the fundus oculi Ef. FIG. 9A shows one example of the feature of scanning of the signal light LS, when the fundus oculi Ef is seen from a direction that the signal light LS enters the eye E (that is, seen from −z side toward +z side in FIG. 1). Further, FIG. 9B shows one example of the feature of arrangement of scanning points (positions at which image measurement is carried out) on each scanning line on the fundus oculi Ef.

As shown in FIG. 9A, the signal light LS is scanned within a rectangular-shaped scanning region R that has been preset. Within the scanning region R, a plurality of (m number of) scanning lines R1 through Rm are set in the x-direction. When the signal light LS is scanned along the respective scanning lines Ri (i=1 through m), detection signals of the interference light LC are generated. For example, the size of the scanning region R is 6 mm×6 mm, and the number of the scanning lines Ri is 256.

A direction of each scanning line Ri will be referred to as the "main scanning direction" and a direction orthogonal thereto will be referred to as the "sub-scanning direction". Scanning of the signal light LS in the main scanning direction is performed by changing the facing direction of the reflecting surface of the Galvano mirror 141A. Scanning in the sub-scanning direction is performed by changing the facing direction of the reflecting surface of the Galvano mirror 141B.

On each scanning line Ri, as shown in FIG. 9B, a plurality of (n number of) scanning points Ri1 through Rin are preset. The number of the scanning points Rij on each scanning line Ri is, for example, 256. By thus setting, several scanning points are set in a region of each stimulating point Pi. At the time of calculation of the layer thickness, the layer thickness is measured in the position of each of the scanning points, and the average value of these several measured values is assumed to be the layer thickness at the stimulating point Pi.

In order to execute the scanning shown in FIGS. 9A and 9B, the controller 210 firstly controls the Galvano mirrors 141A and 141B, and sets the target of the signal light LS entering into the fundus oculi Ef to a scan start position RS (scanning point R11) on a first scanning line R1. Subsequently, the controller 210 controls the low coherence light source 160 to flush the low coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, makes the low coherence light L0 flushed, and makes the signal light LS enter the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in accordance with the interference light LC for each scanning point, by flushing the low coherence light L0 at each scanning point while shifting the incident target of the signal light LS from scanning point R13 to R14, - - - , R1 (n−1), and R1*n* in order.

When the measurement at a last scanning point R1*n* of the first scanning line R1 is finished, the controller 210 controls the Galvano mirrors 141A and 141B simultaneously to shift the incident target of the signal light LS to a first scanning point R21 of a second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of a third scanning line R3, - - - , an m−1th scanning line R(m−1), an mth scanning line Rm to obtain the detection signals corresponding to the respective scanning points. Symbol RE on a scanning line Rm is a scan end position corresponding to a scanning point Rmn.

Consequently, the controller 210 obtains (m×n) number of detection signals corresponding to (m×n) number of scanning points Rij (i=1 through m, j=1 through n) in the scanning region R. Hereinafter, detection signals corresponding to the scanning points Rij may be denoted by Dij.

Such interlocking control of the shift of scanning points and the emission of the low coherence light L0 as described above can be realized by synchronizing, for instance, timing of transmission of control signals to the mirror drive mechanisms 241 and 242 and timing of transmission of control signals to the low coherence light source 160.

As described above, when each of the Galvano mirrors 141A and 141 B is operated, the controller 210 stores the position of the scanning line Ri and the position of the scanning point Rij (coordinates on the x-y coordinate system) as information representing the content of the operation. This stored content (scanning position information) is used in an image forming process as in conventional one.

Next, an example of image processing performed at the time of execution of scan of the signal light LS shown in FIG. 9 is explained.

The image forming part 220 forms a tomographic image of the fundus oculi Ef along each scanning line Ri (main scanning direction). Further, the image processing section 230 forms a 3-dimensional image of the fundus oculi Ef based on the tomographic image formed by the image forming part 220.

The formation process of a tomographic image by the image forming part 220, as in the conventional one, includes a 2-step arithmetic process. In the first step of the arithmetic process, based on the detection signal Dij corresponding to each scanning point Rij, an image in the depth-wise direction (z-direction in FIG. 1) of the fundus oculi Ef at the scanning point Rij is formed.

Figure 10:
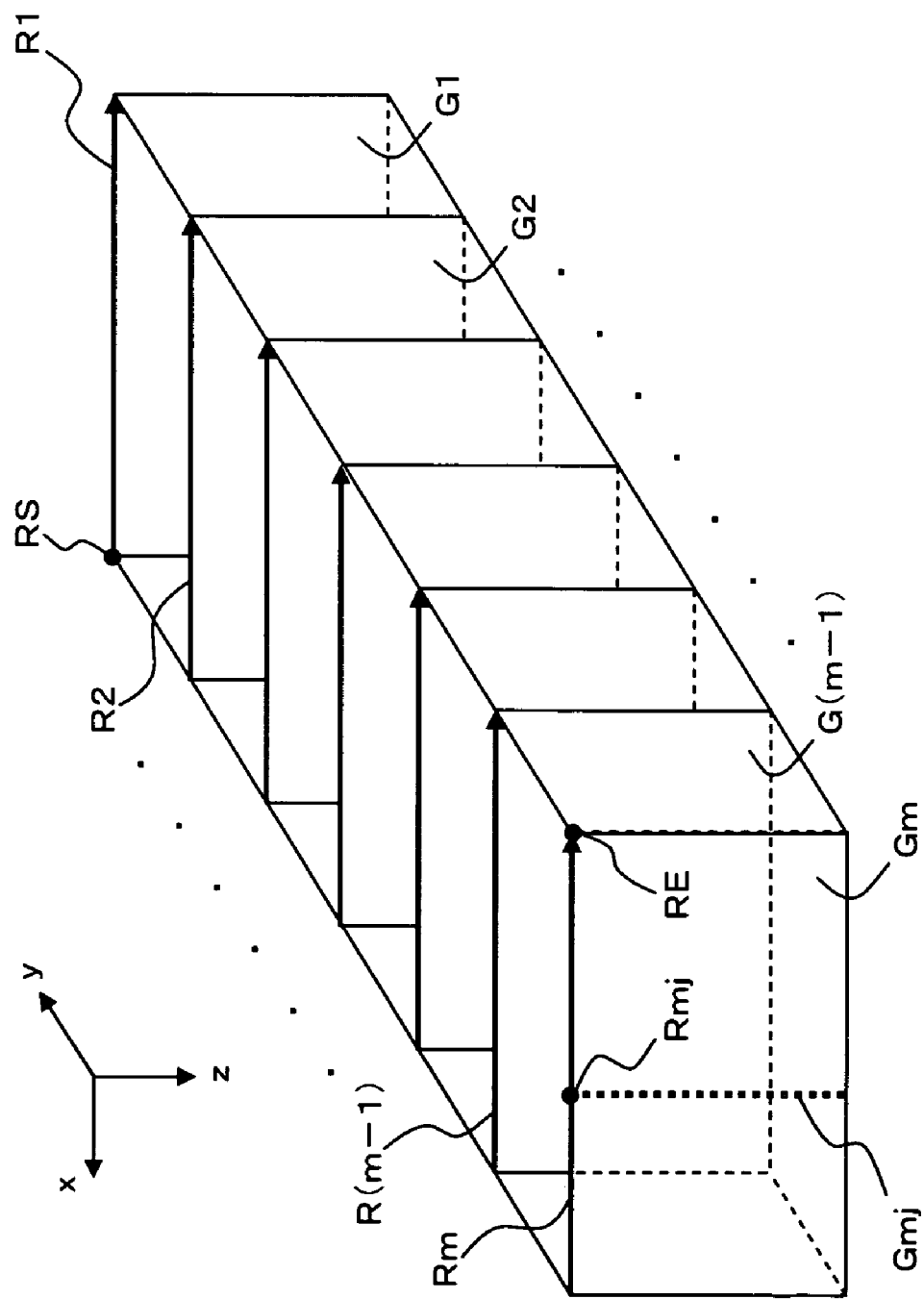
FIG. 10 is a schematic diagram showing one example of the feature of scan of signal light and the feature of a tomographic image formed along each scanning line in the embodiment of the ophthalmologic examination apparatus according to the present invention.

FIG. 10 shows a feature of tomographic images formed by the image forming part 220. In the second step of the arithmetic process, for each scanning line Ri, based on the images in the depth-wise direction at the n number of scanning points Ri1 through Rin on the scanning line Ri, a tomographic image Gi of the fundus oculi Ef along the scanning line Ri is formed. Then, the image forming part 220 determines the arrangement and intervals of the respective scanning points Ri1 through Rin referring to the positional information (scanning position information described before) of the respective scanning points Ri1 through Rin, and forms the scanning line Ri. Through the process described above, m number of tomographic images G1 through Gm at different positions in the sub scanning direction (y direction) are obtained.

Next, the process of forming a 3-dimensional image based on the tomographic images G1 through Gm will be described. The image processor 230 forms a 3-dimensional image of the fundus oculi Ef by performing a known interpolating process to interpolate an image between the adjacent tomographic images Gi and G (i+1).

Then, the image processor 230 determines the arrangement and intervals of the respective scanning lines Ri with reference to the positional information of the respective scanning lines Ri to form this 3-dimensional image. For this 3-dimensional image, 3-dimensional coordinates (x, y, z) are set, based on the positional information (the scanning point coordinate information) of each scanning point Rij and the z-coordinate in the depth-wise image.

Furthermore, based on this 3-dimensional image, the image processor 230 can form a tomographic image of the fundus oculi Ef at a cross-section in any direction other than the main scanning direction (x-direction). When the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

An image Gmj shown in FIG. 10 represents an image in the depth-wise direction (z-direction) at the scanning point Rmj on the scanning line Rm. A depth-wise image at each scanning point Rij on the scanning line Ri formed by the first-step arithmetic process is represented as "image Gij."

Aspects of the scanning of signal light LS by the ophthalmologic examination apparatus 1 are not limited to the above. For example, it is possible to scan the signal light LS in the horizontal direction (x direction) only, to scan the same in the vertical direction (y direction) only, to scan the same in a cross-shaped formation with one line vertical and another horizontal, to scan the same radially, to scan the same in a circular formation, to scan the same concentrically, or to scan the same spirally. In other words, as described above, the scanning unit 141 is configured to be capable of scanning the signal light LS independently in both the x direction and the y direction, so that it is possible to scan the signal light LS along an arbitrary trajectory on the x-y plane.

Usage

Figure 11:
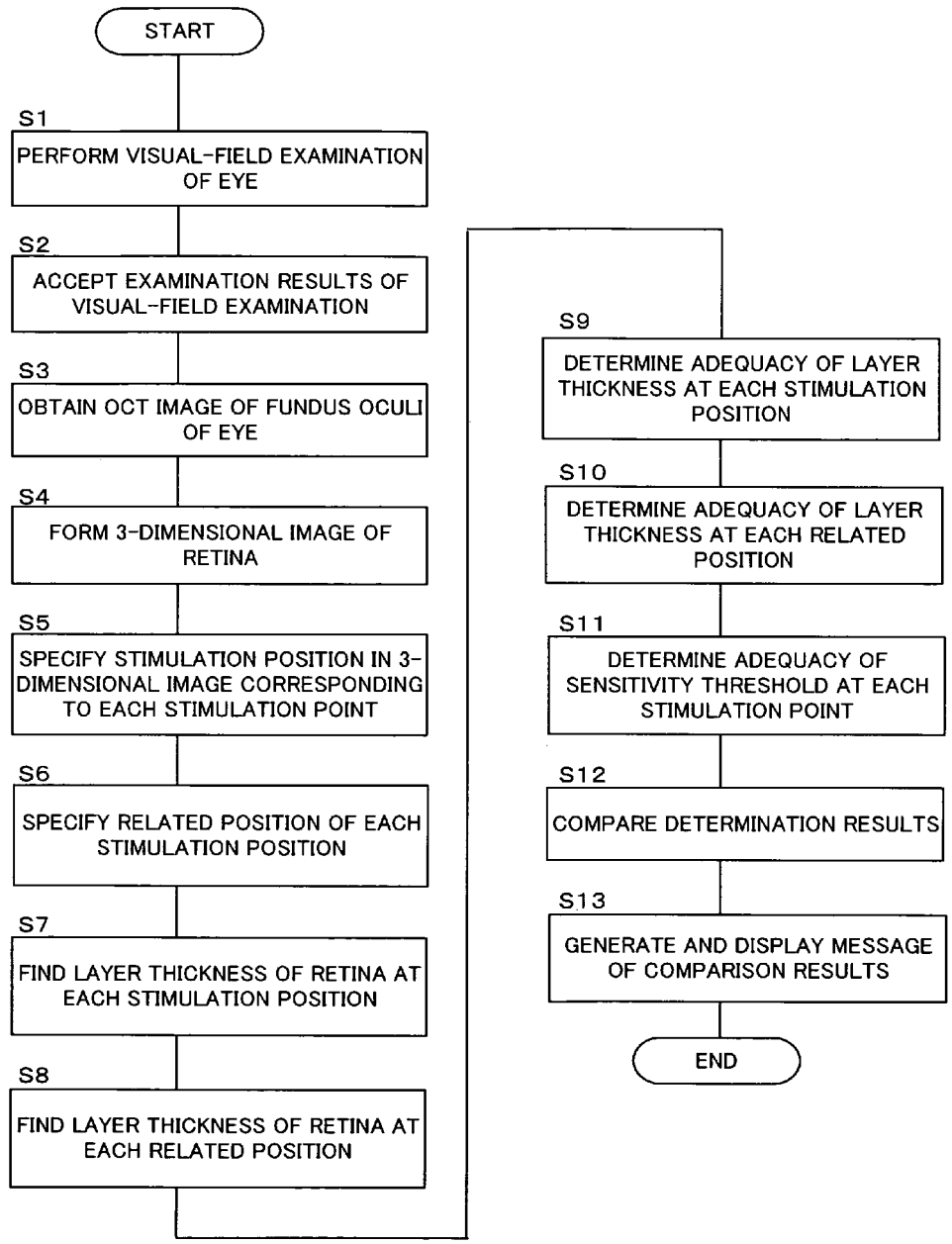
FIG. 11 is a flowchart showing one example of the usage mode of the embodiment of the ophthalmologic examination apparatus according to the present invention.

Usage of the ophthalmologic examination apparatus 1 will be explained. A flowchart in FIG. 11 represents an example of the usage when a visual-field examination is carried out first.

First, a visual-field examination of the eye E is performed by means of a perimeter (not shown) (S1). The stimulation pattern 1000 in FIG. 7 shall be employed in this visual-field examination. The ophthalmologic examination apparatus 1 accepts examination results of the visual-field examination (S2). The controller 210 causes the storage 237 to store the examination results.

Next, an OCT image of the fundus oculi Ef of the eye E is obtained by using the ophthalmologic examination apparatus 1 (S3). Herein, the scan of the signal light LS shown in FIG. 9 is performed for the defined region of the stimulation pattern 1000 to form the tomographic images G1 through Gm shown in FIG. 10. The image processor 230 forms 3-dimensional images that are based on the tomographic images G1 through Gm (S4).

Subsequently, the stimulation-position specifying part 233 specifies, in the 3-dimensional image, a stimulation position corresponding to each stimulation point Pi in the stimulation pattern 1000 (S5). Next, the displacement calculation part 234 specifies a related position of each stimulation position (S6). The examination-position specifying part 231 sends the coordinates of the stimulation position and the coordinates of the related position to the layer-thickness measuring part 235.

The layer-thickness measuring part 235 analyzes the 3-dimensional image to find a layer thickness of the retina at each stimulation position (S7). In addition, the layer-thickness measuring part 235 analyzes the 3-dimensional image to find the layer thickness of the retina at each related position (S8). The layer-thickness measuring part 235 sends the measuring results of the layer thickness to the examination-results comparing part 236.

The examination-results comparing part 236 determines the adequacy of the layer thickness at each stimulation position (S9). In addition, the examination-results comparing part 236 determines the adequacy of the layer thickness at each related position (S10). Moreover, the examination-results comparing part 236 determines the adequacy of the sensitivity threshold at each stimulation point (S11).

Furthermore, the examination-results comparing part 236 compares these determination results (S12). The controller 210 generates a message that is based on the comparison results and causes the display part 240A to display the message (S13).

Incidentally, the ophthalmologic examination apparatus 1 is also capable of displaying an image of the fundus oculi Ef, examination results of a visual-field examination, and measurement results of the layer thickness. Display examples are shown below.

In a first display example, a 2-dimensional image of the surface of the fundus oculi Ef (fundus oculi image Ef'), an accumulated image that is based on the OCT image, and the examination results of the visual-field examination are superimposed and displayed. The fundus oculi image Ef' is imaged by means of the retinal camera unit 1A either before or after the OCT image is obtained. The accumulated image is generated in the abovementioned manner.

Alignment of the fundus oculi image Ef' with the accumulated image can be performed by specifying a predetermined position in each of the fundus oculi image Ef' and the accumulated image (such as the optic papilla and the macular area), and matching these predetermined positions to each other. In addition, the fundus oculi image Ef' and the OCT image are obtained via the same imaging optical system 120, so that the alignment is made easily when the fixed positions of the eye E are identical. The controller 210 performs such an alignment, and makes the accumulated image displayed so as to be superimposed on the fundus oculi image Ef'.

Furthermore, the controller 210 makes an image of the stimulation pattern used in the visual-field examination displayed so as to be superimposed on the accumulated image and, based on the examination results, makes a numeric value of the sensitivity threshold displayed at a position of each stimulation point in the image of the stimulation pattern. Incidentally, instead of displaying the numeric value, it is possible to display information that represents the adequacy of the sensitivity threshold. As an example of this information, it is possible to display a circular image that shows each stimulation point by distinguishing the adequacy of the sensitivity threshold with different colors.

In a second display example, a fundus oculi image Ef', an accumulated image, and measurement results of the layer thickness are displayed in the superimposed state. At this moment, in a similar manner as in the first display example described above, it is possible to display the accumulated image so as to be superimposed on the fundus oculi image Ef', display the image of the stimulation pattern so as to be superimposed on the accumulated image, and display, at the position of each stimulation point, the information that represents the measurement value or adequacy of the layer thickness.

Furthermore, it is possible to combine the first display example and the second display example. Besides, it is also possible to selectively display the display contents included in the first or second display example.

Actions and Advantageous Effects

The actions and advantageous effects of the aforementioned ophthalmologic examination apparatus 1 will be described.

The ophthalmologic examination apparatus 1 has an image forming part configured to project a light onto the fundus oculi, detect the reflected light thereof, and form a 3-dimensional image that represents the morphology of the retina based on the detected results. The image forming part includes, for example, the retinal camera unit 1A, the OCT unit 150, the image forming part 220, and the image processor 230.

Furthermore, the ophthalmologic examination apparatus 1 has the stimulation-position specifying part 233 configured to specify, in the 3-dimensional image, a plurality of stimulation positions that correspond to a plurality of stimulation points Pi in an visual-field examination and the layer-thickness measuring part 235 configured to find the layer thickness of the retina at each stimulation position by analyzing the 3-dimensional image.

According to the ophthalmologic examination apparatus 1, the layer thickness of the retina at a stimulation point in the visual-field examination can be measured, so that it is possible to comprehend the correspondence between the state of the visual-field function and the morphology of the retina.

In addition, according to the ophthalmologic examination apparatus 1, it is possible to specify a new position (related position) related to the stimulation position, and find the layer thickness of the retina at this related position. Herein, "related" means that it includes at least one position that is a path of signals from the cone at the stimulation position. The ophthalmologic examination apparatus 1 adopts, as the related position, a position where the ganglion cell, which receives signals from the cone existing at the stimulation position, exists. Consequently, it is possible to analyze whether the ganglion cell, which relays the signals from the stimulation position, is normal or abnormal, so that when there is an abnormality in the sensitivity threshold at the stimulation position, it is possible to comprehend whether the cause of the abnormality is the ganglion cell or not.

Incidentally, abnormalities of the visual field caused by retinal disease often originate in the cone or the ganglion cell. Therefore, it is assumed that there is not much need for determining the morphologies of the bipolar cells, horizontal cells, and amacrine cells that are between these cells. However, when analyzing the morphology of these intermediate cells, it is possible to specify a position and to measure layer thickness, as is the case with the ganglion cell.

In addition, according to the ophthalmologic examination apparatus 1, it is possible to compare the layer thickness of the retina and the examination results of an visual-field examination, and output the comparison results, so that it is possible to easily understand both the morphology of the retina that is represented by the layer thickness and the functions of the retina that are represented by the examination results of the visual-field examination.

Modification

The configuration described above is merely one example to preferably implement the ophthalmologic examination apparatus according to the present invention. Therefore, any modification may be implemented appropriately within the scope of the present invention.

It is possible to apply an ophthalmologic examination apparatus that, when a position in the 3-dimensional image is designated, would specify a new position related to this designated position and find the layer thickness of the retina at this new position.

This ophthalmologic examination apparatus has a configuration, for example, similar to that of the ophthalmologic examination apparatus 1 of the above embodiment. An operator designates a position in the 3-dimensional image by means of the operation part 240B. In that case, the controller 210 causes the display part 240A to display images such as a 3-dimensional image and a fundus oculi image Ef'. The operator designates a desired position in the image, for example, by a click operation using a mouse. At this designated position, there is a stimulation point in a visual-field examination (an image of a stimulation pattern may be displayed simultaneously).

A new position is specified by the displacement calculation part 234, in a similar manner as in the above embodiment. In addition, the layer thickness of the retina is measured by the layer-thickness measuring part 235, as is the case with the above embodiment. Incidentally, the layer thickness of the retina can also be measured at the position designated by the operator.

According to the ophthalmologic examination apparatus, it is possible to easily comprehend the morphology of the retina at a position related to the position designated by the operator.

When specifying as a new position related to the designated position a position of the ganglion cell, which receives signals from the cone existing at the designated position, it is possible to analyze the morphologies of both the cone and the ganglion cell.

In addition, when designating a stimulation point in a visual-field examination, it is possible to grasp both the state of the visual-field function at the stimulation point and the morphology of the ganglion cell that receives signals from the cone at the stimulation point.

Moreover, when the stimulation pattern in the visual-field examination is known, such as when examination results are obtained previously, it is possible to set a scanning region R so as to include the region of this stimulation pattern, and to further set a scanning line Ri and a scanning point Rij so as to pass through each stimulation point. Consequently, a 3-dimensional image that includes a tomographic image passing through the stimulation point and the region of the stimulation pattern can be surely and easily obtained.

The difference in length of the light path of the signal light LS and the light path of the reference light LR is adjusted by changing the position of the reference mirror 174 in the above embodiment, but techniques for changing the light path length difference is not limited to this. For example, it is possible to change the light path length difference by moving the retinal camera unit 1A and the OCT unit 150 together to the eye E and thereby changing the light path length of the signal light LS. In addition, it is also possible to change the light path length difference by moving the object to be measured in the depth direction (z direction).

The ophthalmologic examination apparatus explained in the above embodiment is configured to include the optical image measuring apparatus of the Fourier Domain type, but optical image measuring apparatuses that can be mounted on an ophthalmologic examination apparatus are not limited to this. For example, it is possible to adopt an ophthalmologic examination apparatus that comprises arbitrary optical image measuring apparatuses such as a Full Field type and Swept Source type.

Ophthalmologic Information-Processing Apparatus

An embodiment of an ophthalmologic information-processing apparatus according to the present invention is explained. The ophthalmologic information-processing apparatus according to this embodiment has a configuration similar to that of the arithmetic and control unit 200 of the abovementioned ophthalmologic examination apparatus 1.

Figure 12:
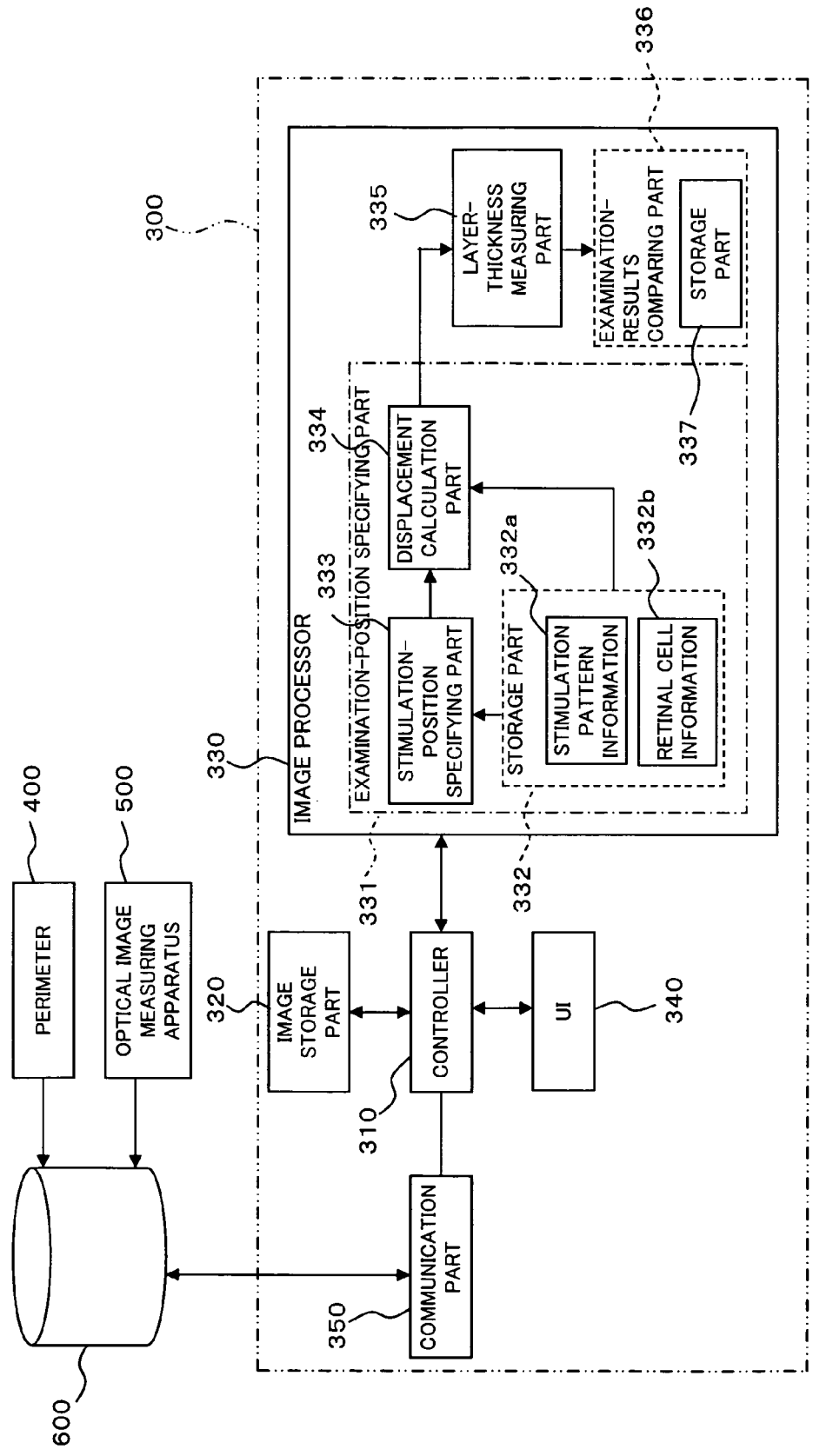
FIG. 12 is a schematic block diagram showing one example of the configuration in the embodiment of the ophthalmologic information-processing apparatus according to the present invention.

A configuration example of the ophthalmologic information-processing apparatus according to the present invention is shown in FIG. 12. An ophthalmologic information-processing apparatus 300 is connected to a database 600 via a communication line such as a LAN. The database 600 is connected to a perimeter 400 via the communication line, and receives and keeps examination results of an examination of a visual field that has been implemented by the perimeter 400. In addition, the database 600 is connected to an optical image measuring apparatus 500 via the communication line, and receives and keeps OCT images that have been obtained by the optical image measuring apparatus 500.

The ophthalmologic information-processing apparatus 300 has a configuration similar to that of a general computer (cf. FIG. 4).

A communication part 350 accepts examination results of an examination of a visual field and an OCT image from the database 600. The communication part 350 is an example of the "accepting part" of the present invention. The communication part 350 sends the accepted examination results of the visual-field examination and OCT image to a controller 310.

The controller 310 stores the examination results of the visual-field examination into storage 337 of an examination-results comparing part 336. In addition, the controller 310 stores the OCT image into image storage 320.

The controller 310 reads out the OCT image from the image storage 320 and sends to an image processor 330. When the OCT image is a tomographic image, the image processor 330 forms a 3-dimensional image based on the tomographic images. The 3-dimensional image is sent to an examination-position specifying part 331. The examination-position specifying part 331 is an example of the "specifying part" of the present invention.

Storage 332 stores stimulation pattern information 332a and retinal cell information 332b that are similar to those in the above embodiment. The storage 332 is an example of the "storing part" of the present invention.

A stimulation-position specifying part 333 specifies, in the 3-dimensional image, a position (stimulation position) that corresponds to each stimulation point included in the stimulation pattern information 332a. A displacement calculation part 334 specifies a position (related position) related to each stimulation point. The related position is, for example, a position where the ganglion cell, which receives signals from the cone existing at the stimulation position, exists.

A layer-thickness measuring part 335 analyzes the 3-dimensional image and thereby measures the layer thickness of the retina at the stimulation position or the related position. The layer-thickness measuring part 335 is an example of the "analyzing part" of the present invention.

An examination-results comparing part 336 compares the layer thickness at the stimulation position, the layer thickness at the related position, and the examination results of the visual-field examination (sensitivity threshold at a stimulation point). The examination-results comparing part 336 is an example of the "comparing part" of the present invention.

The controller 310 generates a message based on the comparison results and causes a user interface 340 to display the message. The user interface 340 includes a display device and an operation device. The user interface 340 (display device) is an example of the "output part" of the present invention.

According to the ophthalmologic information-processing apparatus 300, it is possible to measure the layer thickness of the retina at a stimulation point in the visual-field, so that it is possible to grasp the correspondence between the state of the visual-field function and the morphology of the retina.

Further, according to the ophthalmologic information-processing apparatus 300, it is possible to specify a new position (related position) related to the stimulation position, and find the layer thickness of the retina at this related position. The related position is, for example, a position where the ganglion cell, which receives signals from the cone existing at the stimulation position, exists. Consequently, it is possible to grasp whether the ganglion cell, which relays the signals from the stimulation position, is normal or abnormal, so that when there is an abnormality in the sensitivity threshold at the stimulation position, it is possible to grasp whether the cause of the abnormality is the ganglion cell or not.

Furthermore, according to the ophthalmologic information-processing apparatus 300, it is possible to compare the layer thickness of the retina and the examination results of an visual-field examination, and output the comparison results, so that it is possible to easily grasp both the morphology of the retina that is represented by the layer thickness and the functions of the retina that are represented by the examination results of the visual-field examination.

Another embodiment of the ophthalmologic information-processing apparatus according to the present invention is explained. When a position in a 3-dimensional image is designated, this ophthalmologic information-processing apparatus specifies a new position related to this designated position and finds the layer thickness of the retina at this new position.

For example, this ophthalmologic information-processing apparatus has a configuration similar to that of the aforementioned ophthalmologic information-processing apparatus 300. An operator designates a position in the 3-dimensional image by means of the user interface 340. In that case, the controller 310 causes the user interface 340 to display images such as a 3-dimensional image and a fundus oculi image. The operator designates a desired position in the image, for example, by a click operation using a mouse. As this designated position, there is a stimulation point in a visual-field examination (an image of a stimulation pattern may be displayed simultaneously).

A new position is specified by the displacement calculation part 334, in a similar manner as in the above embodiment. In addition, the layer thickness of the retina is measured by the layer-thickness measuring part 335, as is the case with the above embodiment. Incidentally, the layer thickness of the retina can also be measured at the position designated by the operator.

According to the ophthalmologic information-processing apparatus, it is possible to easily grasp the morphology of the retina at a position related to the position designated by the operator.

When specifying as a new position related to the designated position a position of the ganglion cell, which receives signals from the cone existing at the designated position, it is possible to grasp the morphologies of both the cone and the ganglion cell.

Further, when designating a stimulation point in a visual-field examination, it is possible to grasp both the state of the visual-field function at the stimulation point and the morphology of the ganglion cell that receives signals from the cone at the stimulation point.

The ophthalmologic information-processing apparatus according to the present invention is not limited to those described above, and it is possible to apply any modification within the scope of the present invention when necessary.

For example, an ophthalmologic information-processing apparatus according to the present invention is capable of realizing the various operations described in the explanation of the above ophthalmologic examination apparatus 1.

Program

Herein, a program for controlling the ophthalmologic information-processing apparatus and the ophthalmologic examination apparatus will be explained. The abovementioned control program 204a is an example of the program. Hereinafter, two examples of the program will be explained.

In a first embodiment, the program controls a computer that has a storing part for storing a 3-dimensional image representing the morphology of a retina. Examples of the storing part include the storage 232 and the storage 332 of the above embodiments.

This program makes this computer function as both a specifying part and an analyzing part. The specifying part specifies, in a 3-dimensional image, a plurality of positions that correspond to a plurality of stimulation points in a visual-field examination. Examples of the specifying part include the examination-position specifying part 231 and the examination-position specifying part 331 of the above embodiments.

The analyzing part analyzes the 3-dimensional image to find the layer thickness of the retina at each position that has been specified. Examples of the analyzing part include the layer-thickness measuring part 235 (and the examination-results comparing part 236) and the layer-thickness measuring part 335 (and the examination-results comparing part 336) of the above embodiments.

According to the program, it is possible to measure the layer thickness of the retina at a stimulation point in a visual-field examination, so that it is possible to grasp the correspondence between the state of a visual-field function and the morphology of the retina.

In a second embodiment, the program makes a computer, which has a storing part for storing a 3-dimensional image representing the morphology of a retina, function as a designating part, a specifying part, and an analyzing part. The designating part designates a position in the 3-dimensional image. Examples of the designating part include the user interface 240 (operation part 240B) and the user interface 340 (operation device).

The specifying part specifies a new position related to the designated position. Examples of the specifying part include the examination-position specifying part 231 and the examination-position specifying part 331 of the above embodiments.

The analyzing part analyzes the 3-dimensional image to find the layer thickness of the retina at the new position. Examples of the analyzing part include the layer-thickness measuring part 235 (and the examination-results comparing part 236) and the layer-thickness measuring part 335 (and the examination-results comparing part 336) of the above embodiments.

According to the program, it is possible to easily grasp the morphology of the retina at a position related to the position designated by the operator.

When specifying the position of the ganglion cell, which receives signals from the cone existing at the designated position, as a new position related to the designated position, it is possible to grasp the morphologies of both the cone and the ganglion cell.

In addition, when designating a stimulation point in a visual-field examination, it is possible to grasp both the state of the visual-field function at the stimulation point and the morphology of the ganglion cell that receives signals from the cone at the stimulation point.

The program according to the present invention can be recorded in any recording medium readable by a drive of the computer. For example, it is possible to use a recording medium such as an optical disk, a magneto-optical disk (CD-ROM, DVD-ROM, DVD-ROM, MO, etc.), and a magnetic storage medium (hard disk, Floppy Disk™, ZIP, etc.). Moreover, it is also possible to store the program in a storage device such as a hard disk drive or a memory. Furthermore, it is also possible to transmit the program via a network such as the Internet and a LAN.

What is claimed is:

1. An opthalmologic information-processing apparatus comprising:
    an accepting part configured to accent a 3-dimensional image representing a morphology of a retina;
    a specifying part configured to specify, in the 3-dimensional image, a plurality of positions corresponding to a plurality of stimulation points in a visual-field examination; and
    an analyzing part configured to analyze the 3-dimensional image and find a layer thickness of the retina at each of the plurality of positions,
    wherein the specifying part specifies, for each of the plurality of positions, a new position related to the position,
    wherein the analyzing part analyzes the 3-dimensional image and finds the layer thickness of the retina at the new position,
    wherein the new position is a position where a ganglion cell, which receives signals from a cone existing at the position, exists,
    wherein the specifying part comprises a storing part configured to previously store association information that associates a position of a cone and a position of a ganglion cell, and
    wherein the specifying part refers to the association information, for each of the plurality of positions, and finds the position of the ganglion cell corresponding to the position of the cone, as the new position.

2. An opthalmologic information-processing apparatus comprising:
    an accepting part configured to accept a 3-dimensional image representing a morphology of a retina;
    a designating part configured to designate a position in the 3-dimensional image;
    a specifying part configured to specify a new position related to the designated position; and
    an analyzing part configured to analyze the 3-dimensional image and find a layer thickness of the retina at the new position,
    wherein the new position is a position where ganglion cell, which receives signals from cone existing at the designated position, exists,
    wherein the specifying part comprises a storing part configured to previously store association information that associates a position of a cone and a position of a ganglion cell, and
    wherein the specifying part refers to the association information, and finds the position of the ganglion cell corresponding to the designated position, as the new position.

3. An opthalmologic information-processing apparatus comprising:
    an accepting part configured to accept a 3-dimensional image representing a morphology of a retina;
    a specifying part configured to specify, in the 3-dimensional image, a plurality of positions corresponding to a plurality of stimulation points in a visual-field examination; and
    an analyzing part configured to analyze the 3-dimensional image and find a layer thickness of the retina at each of the plurality of positions,
    wherein the specifying part sets, for each of the plurality of positions, an image region including the position, and
    wherein the analyzing part finds, for the each position, the layer thickness at two or more positions in the image region and finds the layer thickness of the retina at the each position based on the layer thickness at the two or more positions.

4. The opthalmologic information-processing apparatus according to claim 3, wherein the analyzing part finds an average value of the layer thickness at the two or more positions.

5. An opthalmologic information-processing apparatus comprising:
    an accepting part configured to accept a 3-dimensional image representing a morphology of a retina;
    a specifying part configured to specify, in the 3-dimensional image, a plurality of positions corresponding to a plurality of stimulation points in a visual-field examination; and
    an analyzing part configured to analyze the 3-dimensional image and find a layer thickness of the retina at each of the plurality of positions,
    wherein the specifying part specifies, for each of the plurality of positions, a new position related to the position,
    wherein the analyzing part analyzes the 3-dimensional image and finds the layer thickness of the retina at the new position,
    wherein the specifying part sets an image region including the new position; and
    wherein the analyzing part finds the layer thickness at two or more positions in the image region, and finds the layer thickness of the retina at the new position based on the layer thickness at the two or more positions.

6. The opthalmologic information-processing apparatus according to claim 5, wherein the analyzing part finds an average value of the layer thickness at the two or more positions.

7. An opthalmologic information-processing apparatus comprising:
    an accepting part configured to accent a 3-dimensional image representing a morphology of a retina;
    a designating part configured to designate a position in the 3-dimensional image;
    a specifying part configured to specify a new position related to the designated position; and
    an analyzing part configured to analyze the 3-dimensional image and find a layer thickness of the retina at the new position,
    wherein the specifying part sets an image region including the new position, and
    wherein the analyzing part finds the layer thickness at two or more positions in the image region, and finds the layer thickness of the retina at the new position based on the layer thickness at the two or more positions.

8. The opthalmologic information-processing apparatus according to claim 7, wherein the analyzing part finds an average value of the layer thickness at the two or more positions.

9. An opthalmologic information-processing apparatus comprising:
   an accepting part configured to accent a 3-dimensional image representing a morphology of a retina;
   a specifying part configured to specify, in the 3-dimensional image, a plurality of positions corresponding to a plurality of stimulation points in a visual-field examination; and
   an analyzing part configured to analyze the 3-dimensional image and find a layer thickness of the retina at each of the plurality of positions,
   wherein, the accepting part accepts examination results of a visual-field examination,
   wherein the analyzing part comprises a comparing part configured to compare the layer thickness of the retina and the examination results, and
   wherein an output part configured to output the comparison results is provided.

10. An opthalmologic information-processing apparatus comprising:
    an accepting part configured to accept a 3-dimensional image representing a morphology of a retina;
    a designating part configured to designate a position in the 3-dimensional image;
    a specifying part configured to specify a new position related to the designated position; and
    an analyzing part configured to analyze the 3-dimensional image and find a layer thickness of the retina at the new position,
    wherein the accepting part accepts examination results of a visual-field examination,
    wherein the analyzing part comprises a comparing part configured to compare the layer thickness of the retina and the examination results, and
    wherein an output part configured to output the comparison results is provided.

11. An opthalmologic examination apparatus comprising:
    an image forming part configured to project a light onto a fundus oculi, detect the reflected light thereof, and form a 3-dimensional image representing a morphology of a retina based on the detected results;
    a specifying part configured to specify, in the 3-dimensional image, a plurality of positions corresponding to a plurality of stimulation points in a visual-field examination; and
    an analyzing part configured to analyze the 3-dimensional image and find a layer thickness of the retina at each of the plurality of positions.

12. The opthalmologic examination apparatus according to claim 11, wherein the specifying part specifies, for each of the plurality of positions, a new position related to the position, and
    wherein the analyzing part analyzes the 3-dimensional image and finds the layer thickness of the retina at the new position.

* * * * *